(12) United States Patent
Lubenau

(10) Patent No.: US 11,357,842 B2
(45) Date of Patent: Jun. 14, 2022

(54) PD-L1 TARGETING DNA VACCINE FOR CANCER IMMUNOTHERAPY

(71) Applicant: VAXIMM AG, Basel (CH)

(72) Inventor: Heinz Lubenau, Neustadt an der Weinstrasse (DE)

(73) Assignee: Vaximm AG, Basel (CH)

( * ) Notice: Subject to any disclaimer, the term of this patent is extended or adjusted under 35 U.S.C. 154(b) by 0 days.

(21) Appl. No.: 16/494,629

(22) PCT Filed: Mar. 16, 2018

(86) PCT No.: PCT/EP2018/056721
§ 371 (c)(1),
(2) Date: Sep. 16, 2019

(87) PCT Pub. No.: WO2018/167290
PCT Pub. Date: Sep. 20, 2018

(65) Prior Publication Data
US 2020/0085928 A1     Mar. 19, 2020

(30) Foreign Application Priority Data

Mar. 17, 2017   (EP) .................................... 17161666
Sep. 1, 2017    (EP) .................................... 17188941

(51) Int. Cl.
*A61K 39/112*     (2006.01)
*A61K 39/00*      (2006.01)
*C12N 15/74*      (2006.01)

(52) U.S. Cl.
CPC ...... *A61K 39/0011* (2013.01); *A61K 39/0275* (2013.01); *C12N 15/74* (2013.01); *A61K 2039/522* (2013.01); *A61K 2039/523* (2013.01)

(58) Field of Classification Search
None
See application file for complete search history.

(56) References Cited

U.S. PATENT DOCUMENTS

| | | | |
|---|---|---|---|
| 9,273,137 B2* | 3/2016 | Fang | A61P 35/00 |
| 2015/0017194 A1 | 1/2015 | Akahata et al. | |
| 2016/0068801 A1* | 3/2016 | Lubenau | C07K 14/4748 |
| | | | 435/252.3 |

FOREIGN PATENT DOCUMENTS

| | | |
|---|---|---|
| WO | 2013056716 A1 | 4/2013 |
| WO | 2015090584 A1 | 6/2015 |
| WO | 2016202458 A1 | 12/2016 |

OTHER PUBLICATIONS

Wieckowski et al. Third CRI-CIMT-EATI-AACR International Cancer Immunotherapy Conference: Translating Science into Survival, Poster session B, Poster # B057 of Cancer Vaccines and Targets session on Sep. 8, 2017, Mainz, Germany, Sep. 6-9, 2017.*
Niethammer et al. BMC Cancer 12: 361, pp. 1-8, 2012.*
Zhao et al. Acta Med. Univ. Sci. Technol. Huszhong. 35: 490-491, 2006.*
Skolnick et al. Trends in Biotechnology 18: 34-39, 2000.*
Zheng et al. Oncol. Lett. 18: 5399-5407, 2019.*
Keir et al. Ann. Rev. Immunol. 26: 677-704, 2008.*
International Search Report and Written Opinion of the International Searching Authority in related International Application No. PCT/EP2018/056721, dated Jun. 11, 2018 (14 pages).
Shamaila, M. A. et al., "PD-L1 peptide co-stimulation increases immunogenicity of a dendritic cell-based cancer vaccine", Oncoimmunology, 5(8): 1-9 (Aug. 2016).

* cited by examiner

*Primary Examiner* — Sarvamangala Devi
(74) *Attorney, Agent, or Firm* — McNeill Baur PLLC

(57) ABSTRACT

The present invention relates to an attenuated strain of *Salmonella* comprising at least one copy of a DNA molecule comprising an expression cassette encoding PD-L1. In particular, the present invention relates to said attenuated strain of *Salmonella* for use in the treatment of cancer.

14 Claims, 14 Drawing Sheets

Figure 15:
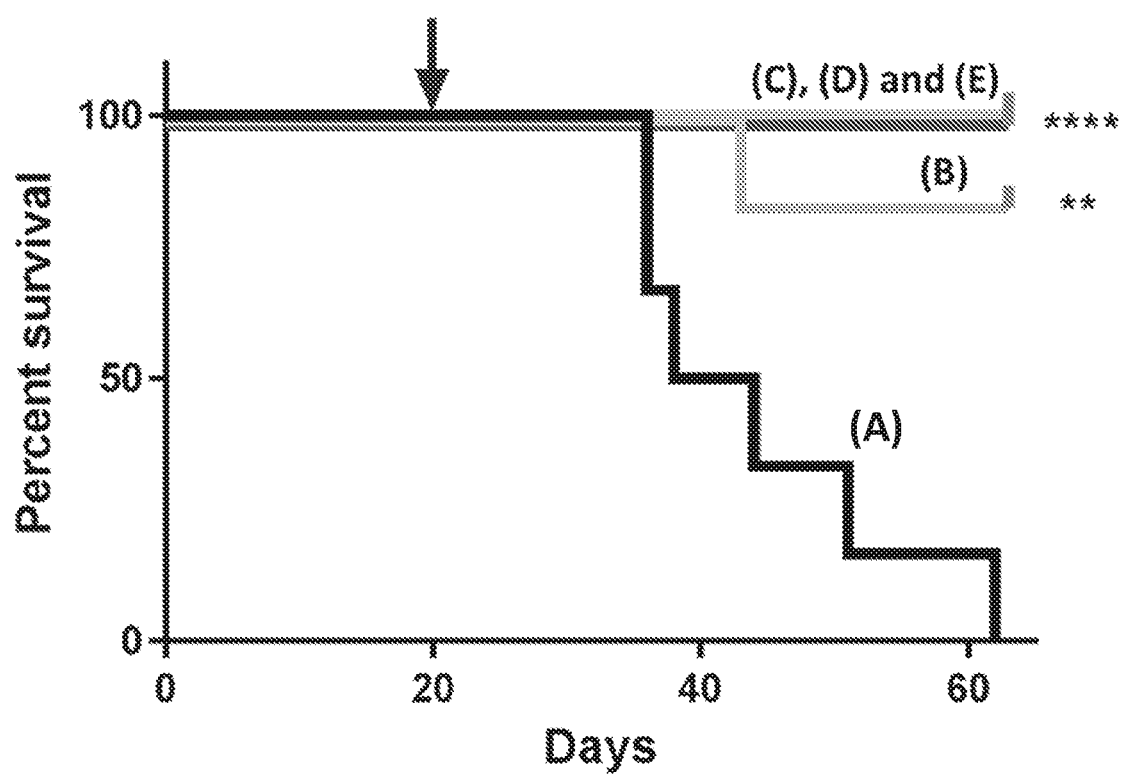

Specification includes a Sequence Listing.

Figure 1

MRIFAVFIFMTYWHLLNAFTVTVPKDLYVVEYGSNMTIECKFPVEKQLDLAALIVYWEME
DKNIIQFVHGEEDLKVQHSSYRQRARLLKDQLSLGNAALQITDVKLQDAGVYRCMISYG
GADYKRITVKVNAPYNKINQRILVVDPVTSEHELTCQAEGYPKAEVIWTSSDHQVLSGKT
TTTNSKREEKLFNVTSTLRINTTTNEIFYCTFRRLDPEENHTAELVIPELPLAHPPNERTH
LVILGAILLCLGVALTFIFRLRKGRMMDVKKCGIQDTNSKKQSDTHLEET

Figure 2

MFTVTVPKDLYVVEYGSNMTIECKFPVEKQLDLAALIVYWEMEDKNIIQFVHGEEDLKVQ
HSSYRQRARLLKDQLSLGNAALQITDVKLQDAGVYRCMISYGGADYKRITVKVNAPYNK
INQRILVVDPVTSEHELTCQAEGYPKAEVIWTSSDHQVLSGKTTTTNSKREEKLFNVTST
LRINTTTNEIFYCTFRRLDPEENHTAELVIPELPLAHPPNERTHLVILGAILLCLGVALTFIF
RLRKGRMMDVKKCGIQDTNSKKQSDTHLEET

Figure 3

ATGAGGATATTTGCTGTCTTTATATTCATGACCTACTGGCATTTGCTGAACGCATTTA
CTGTCACGGTTCCCAAGGACCTATATGTGGTAGAGTATGGTAGCAATATGACAATTG
AATGCAAATTCCCAGTAGAAAAACAATTAGACCTGGCTGCACTAATTGTCTATTGGG
AAATGGAGGATAAGAACATTATTCAATTTGTGCATGGAGAGGAAGACCTGAAGGTTC
AGCATAGTAGCTACAGACAGAGGGCCCGGCTGTTGAAGGACCAGCTCTCCCTGGG
AAATGCTGCACTTCAGATCACAGATGTGAAATTGCAGGATGCAGGGGTGTACCGCT
GCATGATCAGCTATGGTGGTGCCGACTACAAGCGAATTACTGTGAAAGTCAATGCC
CCATACAACAAAATCAACCAAAGAATTTTGGTTGTGGATCCAGTCACCTCTGAACAT
GAACTGACATGTCAGGCTGAGGGCTACCCCAAGGCCGAAGTCATCTGGACAAGCA
GTGACCATCAAGTCCTGAGTGGTAAGACCACCACCACCAATTCCAAGAGAGGAG
AAGCTTTTCAATGTGACCAGCACACTGAGAATCAACACAACAACTAATGAGATTTTC
TACTGCACTTTTAGGAGATTAGATCCTGAGGAAAACCATACAGCTGAATTGGTCATC
CCAGAACTACCTCTGGCACATCCTCCAAATGAAAGGACTCACTTGGTAATTCTGGGA
GCCATCTTATTATGCCTTGGTGTAGCACTGACATTCATCTTCCGTTTAAGAAAGGG
AGAATGATGGATGTGAAAAATGTGGCATCCAAGATACAAACTCAAAGAAGCAAAGT
GATACACATTTGGAGGAGACGTAA

Figure 4

ATGTTTACTGTCACGGTTCCCAAGGACCTATATGTGGTAGAGTATGGTAGCAATATG
ACAATTGAATGCAAATTCCCAGTAGAAAAACAATTAGACCTGGCTGCACTAATTGTC
TATTGGGAAATGGAGGATAAGAACATTATTCAATTTGTGCATGGAGAGGAAGACCTG
AAGGTTCAGCATAGTAGCTACAGACAGAGGGCCCGGCTGTTGAAGGACCAGCTCT
CCCTGGGAAATGCTGCACTTCAGATCACAGATGTGAAATTGCAGGATGCAGGGGTG
TACCGCTGCATGATCAGCTATGGTGGTGCCGACTACAAGCGAATTACTGTGAAAGT
CAATGCCCCATACAACAAAATCAACCAAAGAATTTTGGTTGTGGATCCAGTCACCTC
TGAACATGAACTGACATGTCAGGCTGAGGGCTACCCCAAGGCCGAAGTCATCTGGA
CAAGCAGTGACCATCAAGTCCTGAGTGGTAAGACCACCACCACCAATTCCAAGAGA
GAGGAGAAGCTTTTCAATGTGACCAGCACACTGAGAATCAACACAACAACTAATGA
GATTTTCTACTGCACTTTTAGGAGATTAGATCCTGAGGAAAACCATACAGCTGAATT
GGTCATCCCAGAACTACCTCTGGCACATCCTCCAAATGAAGGACTCACTTGGTAAT
TCTGGGAGCCATCTTATTATGCCTTGGTGTAGCACTGACATTCATCTTCCGTTTAAG
AAAAGGGAGAATGATGGATGTGAAAAAATGTGGCATCCAAGATACAAACTCAAAGAA
GCAAAGTGATACACATTTGGAGGAGACGTAA

Figure 5

TGGGCTTTTGCTGGCCTTTTGCTCACATGTTCTTGACTCTTCGCGATGTACGGGCCA
GATATACGCGTTGACATTGATTATTGACTAGTTATTAATAGTAATCAATTACGGGGTC
ATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTC
CCATAGTAACGCCAATAGGGACTTTCCATTGACGTCAATGGGTGGACTATTTACGGT
AAACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATGG
GACTTTCCTACTTGGCAGTACATCTACGTATTAGTCATCGCTATTACCATGGTGATG
CGGTTTTGGCAGTACATCAATGGGCGTGGATAGCGGTTTGACTCACGGGGATTTCC
AAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGT
GTACGGTGGGAGGTCTATATAAGCAGAGCTCTCTGGCTAACTAGAGAACCCACTGC
TTACTGGCTTATCGAAATTAATACGACTCACTATAGGGAGACCCAAGCTGGCTAGCC
TCGAGTCTAGAGGGCCCGTTTAAACCCGCTGATCAGCCTCGACTGTGCCTTCTAGT
TGCCAGCCATCTGTTGTTTGCCCCTCCCCGTGCCTTCCTTGACCCTGGAAGGTGC
CACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTG
GGAAGACAATAGCAGGCATGCTGGGGATGCGGTGGGCTCTATGGCTTCTACTGGG
CGGTTTTATGGACAGCAAGCGAACCGGAATTGCCAGCTGGGGCGCCCTCTGGTAA
GGTTGGGAAGCCCTGCAAAGTAAACTGGATGGCTTTCTCGCCGCCAAGGATCTGAT
GGCGCAGGGGATCAAGCTCTGATCAAGAGACAGGATGAGGATCGTTTCGCATGATT
GAACAAGATGGATTGCACGCAGGTTCTCCGGCCGCTTGGGTGGAGAGGCTATTCG

Figure 5 (cont.)

GCTATGACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTGCCCTG
AATGAACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTGCTATT
GGGCGAAGTGCCGGGGCAGGATCTCCTGTCATCTCACCTTGCTCCTGCCGAGAAA
GTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAA
GCCGGTCTTGTCGATCAGGATGATCTGGACGAAGAGCATCAGGGGCTCGCGCCAG
CCGAACTGTTCGCCAGGCTCAAGGCGAGCATGCCCGACGGCGAGGATCTCGTCGT
GACCCATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCGTT
GGCTACCCGTGATATTGCTGAAGAGCTTGGCGGCGAATGGGCTGACCGCTTCCTC
GTGCTTTACGGTATCGCCGCTCCCGATTCGCAGCGCATCGCCTTCTATCGCCTTCT
TGACGAGTTCTTCTGAATTATTAACGCTTACAATTTCCTGATGCGGTATTTTCTCCTT
ACGCATCTGTGCGGTATTTCACACCGCATACAGGTGGCACTTTTCGGGGAAATGTG
CGCGGAACCCCTATTTGTTTATTTTTCTAAATACATTCAAATATGTATCCGCTCATGA
GACAATAACCCTGATAAATGCTTCAATAATAGCACGTGCTAAAACTTCATTTTTAATT
TAAAAGGATCTAGGTGAAGATCCTTTTTGATAATCTCATGACCAAAATCCCTTAACGT
GAGTTTTCGTTCCACTGAGCGTCAGACCCCCATCAGTGACCAAACAGGAAAAAACC
GCCCTTAACATGGCCCGCTTTATCAGAAGCCAGACATTAACGCTTCTGGAGAAACT
CAACGAGCTGGACGCGGATGAACAGGCAGACATCTGTGAATCGCTTCACGACCAC
GCTGATGAGCTTTACCGCAGCTGCCTCGCGCGTTTCGGTGATGACGGTGAAAACCT
CTGACACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGGGCGCA
GCCATGACCCAGTCACGTAGCGATAGCGGAGTGTATACTGGCTTAACTATGCGGCA
TCAGAGCAGATTGTACTGAGAGTGCACCATATGCGGTGTGAAATACCGCACAGATG
CGTAAGGAGAAAATACCGCATCAGGCGCTCTTCCGCTTCCTCGCTCACTGACTCGC
TGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTC
CGCCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTC
GCTCCAAGCTGGGCTGTGTGCACGAACCCCCGTTCAGCCCGACCGCTGCGCCTT
ATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTG
CGCTCTGCTGAAGCCAGTTACCTTCGGAAAAGAGTTGGTAGCTCTTGATCCGGCA
AACAAACCACCGCTGGTAGCGGTGGTTTTTTTGTTTGCAAGCAGCAGATTACGCGC
AGAAAAAAAGGATCTCAAGAAGATCCTTTGATC

Figure 6

```
             10         20         30         40         50         60
      MGSDVRDLNA LLPAVPSLGG GGGCALPVSG AAQWAPVLDF APPGASAYGS LGGPAPPPAP 70         80         90        100        110        120
      PPPPPPPPHS FIKQEPSWGG AEPHEEQCLS AFTVHFSGQF TGTAGACRYG PFGPPPPSQA 130        140        150        160        170        180
      SSGQARMFPN APYLPSCLES QPAIRNQGYS TVTFDGTPSY GHTPSHHAAQ FPNHSFKHED 190        200        210        220        230        240
      PMGQQGSLGE QQYSVPPPVY GCHTPTDSCT GSQALLLRTP YSSDNLYQMT SQLECMTWNQ 250        260        270        280        290        300
      MNLGATLKGV AAGSSSSVKW TEGQSNHSTG YESDNHTTPI LCGAQYRIHT HGVFRGIQDV 310        320        330        340        350        360
      RRVPGVAPTL VRSASETSEK RPFMCAYPGC NKRYFKLSHL QMHSRKHTGE KPYQCDFKDC

370
      ERRFSRSDQL K
```

Figure 7

MALPTARPLLGSCGTPALGSLLFLLFSLGWVQPSRTLAGETGQEAAPLDGVLANPPNISSLS
PRQLLGFPCAEVSGLSTERVRELAVALAQKNVKLSTEQLRCLAHRLSEPPEDLDALPLDLLL
FLNPDAFSGPQACTRFFSRITKANVDLLPRGAPERQRLLPAALACWGVRGSLLSEADVRAL
GGLACDLPGRFVAESAEVLLPRLVSCPGPLDQDQQEAARAALQGGGPPYGPPSTWSVST
MDALRGLLPVLGQPIIRSIPQGIVAAWRQRSSRDPSWRQPERTILRPRFRREVEKTACPSGK
KAREIDESLIFYKKWELEACVDAALLATQMDRVNAIPFTYEQLDVLKHKLDELYPQGYPESVI
QHLGYLFLKMSPEDIRKWNVTSLETLKALLEVNKGHEMSPQAPRRPLPQVATLIDRFVKGR
GQLDKDTLDTLTAFYPGYLCSLSPEELSSVPPSSIWAVRPQDLDTCDPRQLDVLYPKARLAF
QNMNGSEYFVKIQSFLGGAPTEDLKALSQQNVSMDLATFMKLRTDAVLPLTVAEVQKLLGP
HVEGLKAEERHRPVRDWILRQRQDDLDTLGLGLQGGIPNGYLVLDLSMQEALSGTPCLLGP
GPVLTVLALLLASTLA

Figure 8

MESPSAPPHRWCIPWQRLLLTASLLTFWNPPTTAKLTIESTPFNVAEGKEVLLLVHNLP
QHLFGYSWYKGERVDGNRQIIGYVIGTQQATPGPAYSGREIIYPNASLLIQNIIQNDTGFY
TLHVIKSDLVNEEATGQFRVYPELPKPSISSNNSKPVEDKDAVAFTCEPETQDATYLWW
VNNQSLPVSPRLQLSNGNRTLTLFNVTRNDTASYKCETQNPVSARRSDSVILNVLYGPD
APTISPLNTSYRSGENLNLSCHAASNPPAQYSWFVNGTFQQSTQELFIPNITVNNSGSY
TCQAHNSDTGLNRTTVTTITVYAEPPKPFITSNNSNPVEDEDAVALTCEPEIQNTTYLW
WVNNQSLPVSPRLQLSNDNRTLTLLSVTRNDVGPYECGIQNKLSVDHSDPVILNVLYGP
DDPTISPSYTYYRPGVNLSLSCHAASNPPAQYSWLIDGNIQQHTQELFISNITEKNSGLY
TCQANNSASGHSRTTVKTITVSAELPKPSISSNNSKPVEDKDAVAFTCEPEAQNTTYLW
WVNGQSLPVSPRLQLSNGNRTLTLFNVTRNDARAYVCGIQNSVSANRSDPVTLDVLYG
PDTPIISPPDSSYLSGANLNLSCHSASNPSPQYSWRINGIPQQHTQVLFIAKITPNNNGTY
ACFVSNLATGRNNSIVKSITVSASGTSPGLSAGATVGIMIGVLVGVALI

Figure 9

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRKRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQPKRRRHRQDALPGPCIASTPKKHRG

Figure 10

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRNRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQPKRRRHRQDALPGPCIASTPKKHRG

Figure 11

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRNRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQ

Figure 12

```
                10         20         30         40         50         60
        MQSKVLLAVA LWLCVETRAA SVGLPSVSLD LPRLSIQKDI LTIKANTTLQ ITCRGQRDLD 70         80         90        100        110        120
        WLWPNNQSGS EQRVEVTECS DGLFCKTLTI PKVIGNDTGA YKCFYRETDL ASVIYVYVQD 130        140        150        160        170        180
        YRSPFIASVS DQHGVVYITE NKNKTVVIPC LGSISNLNVS LCARYPEKRF VPDGNRISWD 190        200        210        220        230        240
        SKKGFTIPSY MISYAGMVFC EAKINDESYQ SIMYIVVVG  YRIYDVVLSP SHGIELSVGE 250        260        270        280        290        300
        KLVLNCTART ELNVGIDFNW EYPSSKHQHK KLVNRDLKTQ SGSEMKKFLS TLTIDGVTRS 310        320        330        340        350        360
        DQGLYTCAAS SGLMTKKNST FVRVHEKPFV AFGSGMESLV EATVGERVRI PAKYLGYPPP 370        380        390        400        410        420
        EIKWYKNGIP LESNHTIKAG HVLTIMEVSE RDTGNYTVIL TNPISKEKQS HVVSLVVYVP 430        440        450        460        470        480
        PQIGEKSLIS PVDSYQYGTT QTLTCTVYAI PPPHHIHWYW QLEEECANEP SQAVSVTNPY 490        500        510        520        530        540
        PCEEWRSVED FQGGNKIEVN KNQFALIEGK NKTVSTLVIQ AANVSALYKC EAVNKVGRGE 550        560        570        580        590        600
        RVISFHVTRG PEITLQPDMQ PTEQESVSLW CTADRSTFEN LTWYKLGPQP LPIHVGELPT
```

Figure 12 (contd.)

```
         610        620        630        640        650        660
   PVCKNLDTLW KLNATMFSNS TNDILIMELK NASLQDQGDY VCLAQDRKTK KRHCVVRQLT 670        680        690        700        710        720
   VLERVAPTIT GNLENQTTSI GESIEVSCTA SGNPPPQIMW FKDNETLVED SGIVLKDGNR.

730        740        750        760        770        780
   NLTIRRVRKE DEGLYTCQAC SVLGCAKVEA FFIIEGAQEK TNLEIIILVG TAVIAMFFWL 790        800        810        820        830        840
   LLVIILRTVK RANGGELKTG YLSIVMDPDE LPLDEHCERL PYDASKWEFP RDRLKLGKPL 850        860        870        880        890        900
   GRGAFGQVIE ADAFGIDKTA TCRTVAVKML KEGATHSEHR ALMSELKILI HIGHHLNVVN 910        920        930        940        950        960
   LLGACTKPGG PLMVIVEFCK FGNLSTYLRS KRNEFVPYKT KGARFRQGKD YVGAIPVDLK 970        980        990       1000       1010       1020
   RRLDSITSSQ SSASSGFVEE KSLSDVEEEE APEDLYKDFL TLEHLICYSF QVAKGMEFLA 1030       1040       1050       1060       1070       1080
   SRKCIHRDLA ARNILLSEKN VVKICDFGLA RDIYKDPDYV RKGDARLPLK WMAPETIFDR 1090       1100       1110       1120       1130       1140
   VYTIQSDVWS FGVLLWEIFS LGASPYPGVK IDEEFCRRLK EGTRMRAPDY TTPEMYQTML 1150       1160       1170       1180       1190       1200
   DCWHGEPSQR PTFSELVEHL GNLLQANAQQ DGKDYIVLPI SETLSMEEDS GLSLPTSPVS
```

Figure 12 (contd.)

```
          1210        1220        1230        1240        1250        1260
     CMEEEEVCDP  KFHYDNTAGI  SQYLQNSKRK  SRPVSVKTFE  DIPLEEPEVK  VIPDDNQTDS 1270        1280        1290        1300        1310        1320
     GMVLASEEELK TLEDRTKLSP  SFGGMVPSKS  RESVASEGSN  QTSGYQSGYH  SDDTDTTVYS 1330        1340        1350
     SEEAELLKLI  EIGVQTGSTA  QILQPDSGTT  LSSPPV
```

Figure 13

MRIFAVFIFMTYWHLLNAFTVTVPKDLYVVEYGSNMTIECKFPVEKQLDLAALIVYWEME
DKNIIQFVHGEEDLKVQHSSYRQRARLLKDQLSLGNAALQITDVKLQDAGVYRCMISYG
GADYKRITVKVNAPYNKINQRILVVDPVTSEHELTCQAEGYPKAEVIWTSSDHQVLSGKT
TTTNSKREEKLFNVTSTLRINTTTNEIFYCTFRRLDPEENHTAELVIPELPLAHPPNER

Figure 14

ATGAGGATATTTGCTGTCTTTATATTCATGACCTACTGGCATTTGCTGAACGCATTTA
CTGTCACGGTTCCCAAGGACCTATATGTGGTAGAGTATGGTAGCAATATGACAATTG
AATGCAAATTCCCAGTAGAAAAACAATTAGACCTGGCTGCACTAATTGTCTATTGGG
AAATGGAGGATAAGAACATTATTCAATTTGTGCATGGAGAGGAAGACCTGAAGGTTC
AGCATAGTAGCTACAGACAGAGGGCCCGGCTGTTGAAGGACCAGCTCTCCCTGGG
AAATGCTGCACTTCAGATCACAGATGTGAAATTGCAGGATGCAGGGGTGTACCGCT
GCATGATCAGCTATGGTGGTGCCGACTACAAGCGAATTACTGTGAAAGTCAATGCC
CCATACAACAAAATCAACCAAAGAATTTTGGTTGTGGATCCAGTCACCTCTGAACAT
GAACTGACATGTCAGGCTGAGGGCTACCCCAAGGCCGAAGTCATCTGGACAAGCA
GTGACCATCAAGTCCTGAGTGGTAAGACCACCACCACCAATTCCAAGAGAGAGGAG
AAGCTTTTCAATGTGACCAGCACACTGAGAATCAACACAACAACTAATGAGATTTTC
TACTGCACTTTTAGGAGATTAGATCCTGAGGAAAACCATACAGCTGAATTGGTCATC
CCAGAACTACCTCTGGCACATCCTCCAAATGAAAGGTAA

Figure 17
A
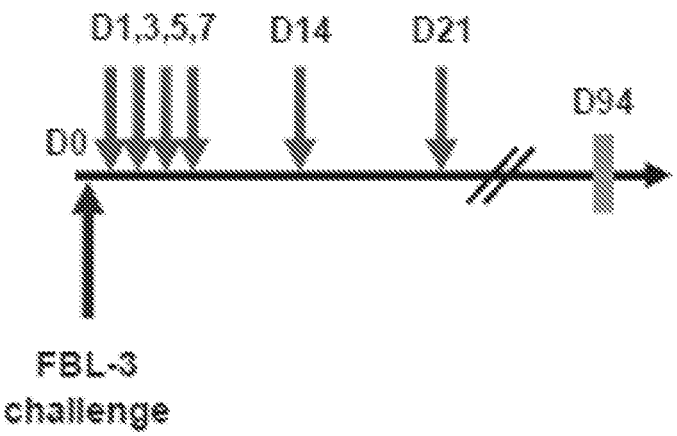
B
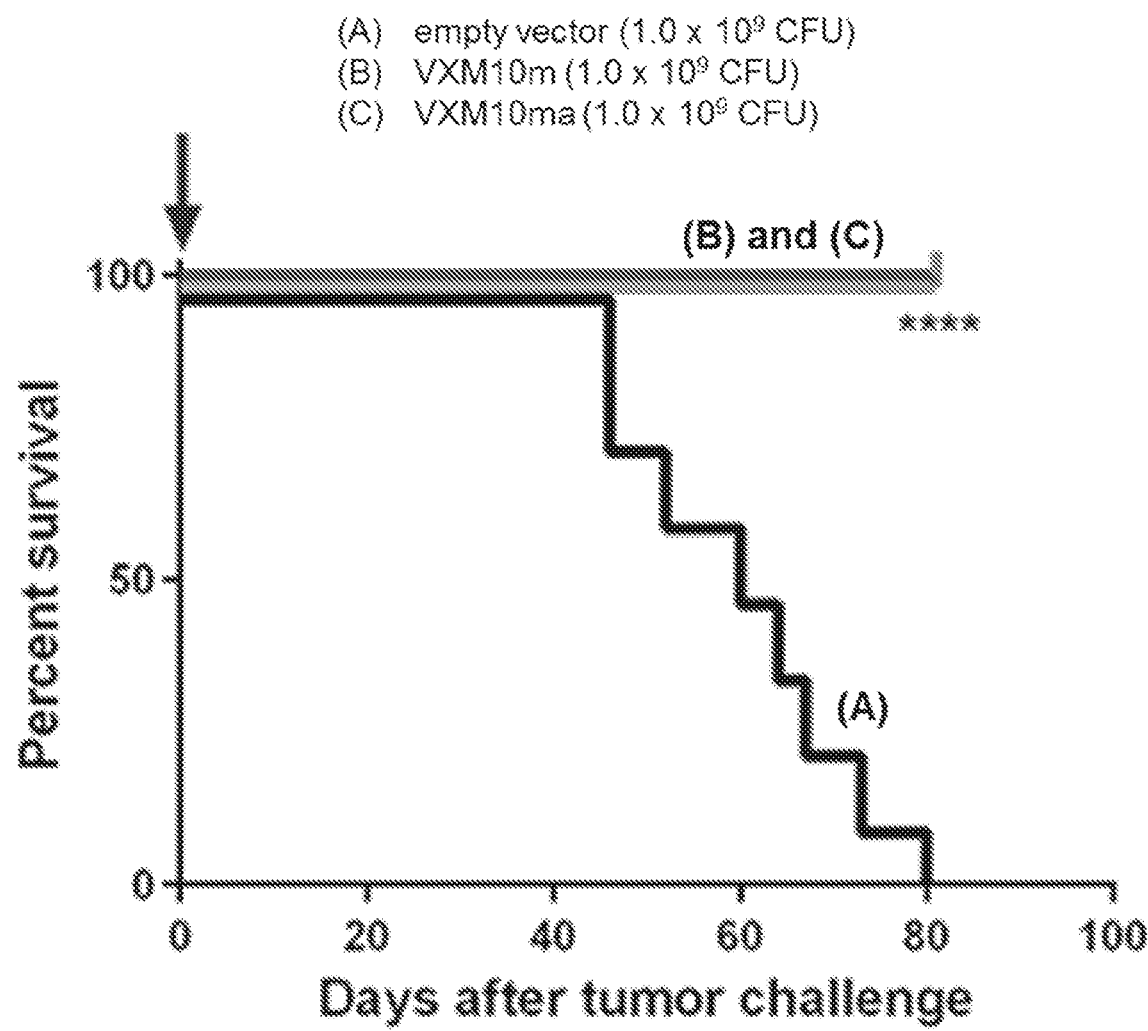

Figure 18
A
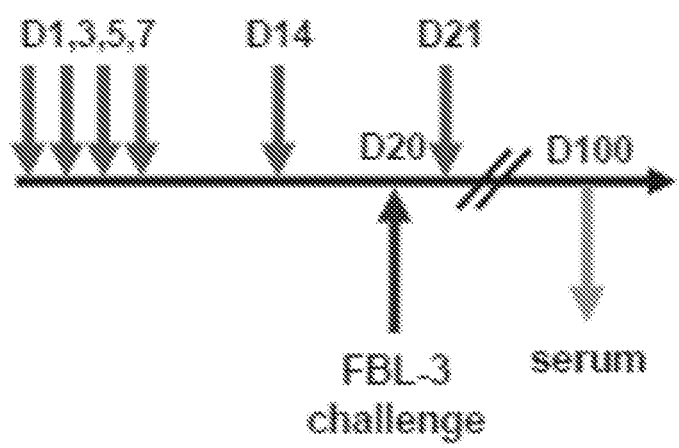
B
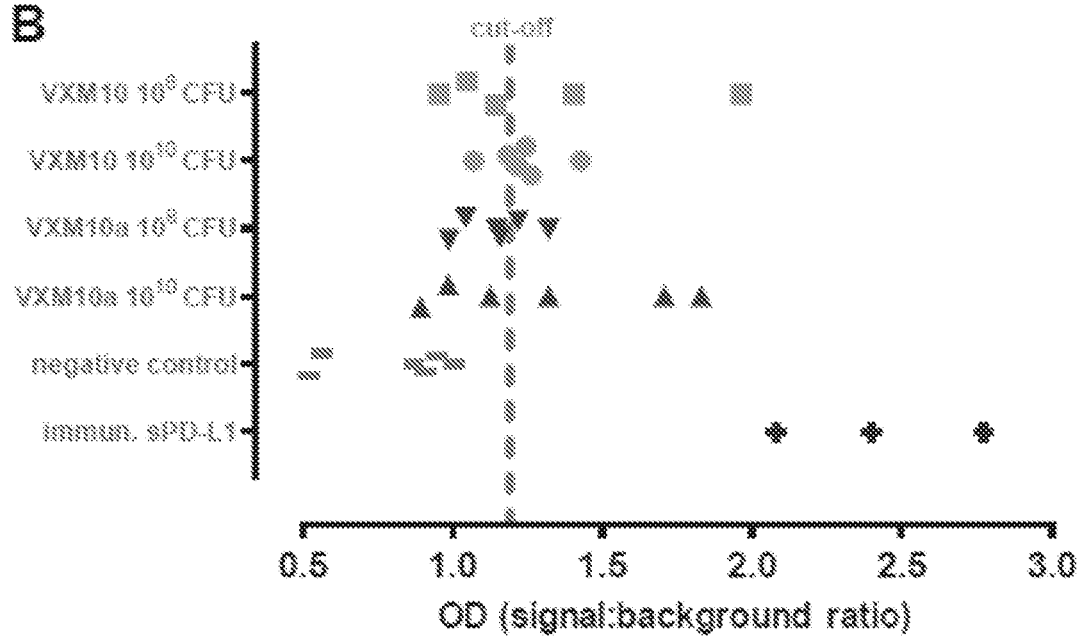

Figure 19
A
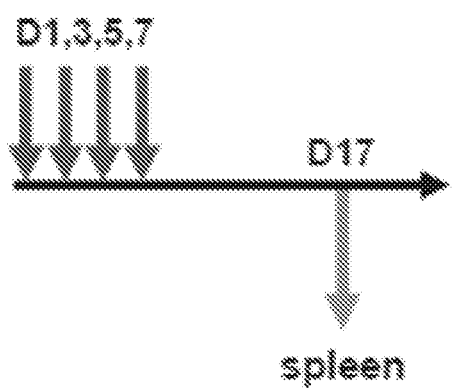
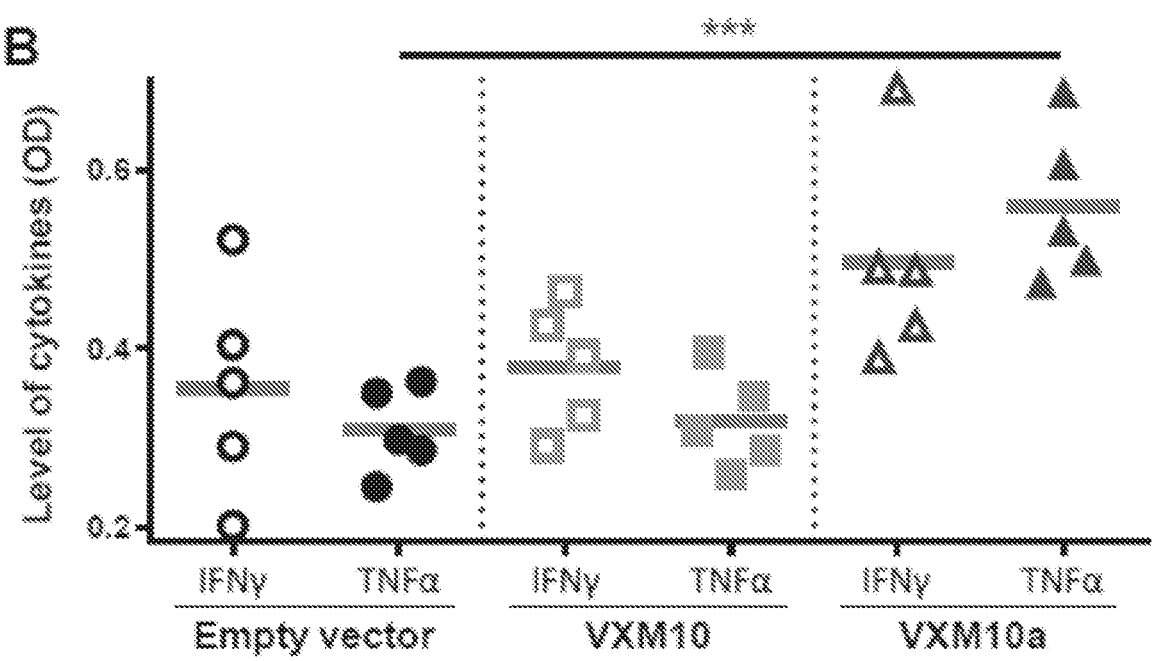

SEQUENCE LISTING

```
<160> NUMBER OF SEQ ID NOS: 19

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
```

```
            260                 265                 270
Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 273
<212> TYPE: PRT
<213> ORGANISM: Homo sapiens

<400> SEQUENCE: 2

Met Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
        115                 120                 125

Pro Val Thr Ser Glu His Glu Leu Thr Cys Gln Ala Glu Gly Tyr Pro
    130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
        195                 200                 205

Ile Pro Glu Leu Pro Leu Ala His Pro Pro Asn Glu Arg Thr His Leu
    210                 215                 220

Val Ile Leu Gly Ala Ile Leu Leu Cys Leu Gly Val Ala Leu Thr Phe
225                 230                 235                 240

Ile Phe Arg Leu Arg Lys Gly Arg Met Met Asp Val Lys Lys Cys Gly
                245                 250                 255

Ile Gln Asp Thr Asn Ser Lys Lys Gln Ser Asp Thr His Leu Glu Glu
            260                 265                 270

Thr

<210> SEQ ID NO 3
<211> LENGTH: 873
<212> TYPE: DNA
<213> ORGANISM: Homo sapiens

<400> SEQUENCE: 3
atgaggatat tgctgtctct tatattcatg acctactggc atttgctgaa cgcatttact        60
```

| gtcacggttc | ccaaggacct | atatgtggta | gagtatggta | gcaatatgac | aattgaatgc | 120 |
| aaattcccag | tagaaaaaca | attagacctg | gctgcactaa | ttgtctattg | ggaaatggag | 180 |
| gataagaaca | ttattcaatt | tgtgcatgga | gaggaagacc | tgaaggttca | gcatagtagc | 240 |
| tacagacaga | gggcccggct | gttgaaggac | cagctctccc | tgggaaatgc | tgcacttcag | 300 |
| atcacagatg | tgaaattgca | ggatgcaggg | gtgtaccgct | gcatgatcag | ctatggtggt | 360 |
| gccgactaca | gcgaattac | tgtgaaagtc | aatgccccat | acaacaaaat | caaccaaaga | 420 |
| attttggttg | tggatccagt | cacctctgaa | catgaactga | catgtcaggc | tgagggctac | 480 |
| cccaaggccg | aagtcatctg | gacaagcagt | gaccatcaag | tcctgagtgg | taagaccacc | 540 |
| accaccaatt | ccaagagaga | ggagaagctt | ttcaatgtga | ccagcacact | gagaatcaac | 600 |
| acaacaacta | atgagatttt | ctactgcact | tttaggagat | tagatcctga | ggaaaaccat | 660 |
| acagctgaat | tggtcatccc | agaactacct | ctggcacatc | ctccaaatga | aaggactcac | 720 |
| ttggtaattc | tgggagccat | cttattatgc | cttggtgtag | cactgacatt | catcttccgt | 780 |
| ttaagaaaag | ggagaatgat | ggatgtgaaa | aatgtggca | tccaagatac | aaactcaaag | 840 |
| aagcaaagtg | atacacattt | ggaggagacg | taa | | | 873 |

<210> SEQ ID NO 4
<211> LENGTH: 822
<212> TYPE: DNA
<213> ORGANISM: Homo sapiens

<400> SEQUENCE: 4

| atgtttactg | tcacggttcc | caaggaccta | tatgtggtag | agtatggtag | caatatgaca | 60 |
| attgaatgca | aattcccagt | agaaaaacaa | ttagacctgg | ctgcactaat | tgtctattgg | 120 |
| gaaatggagg | ataagaacat | tattcaattt | gtgcatggaa | ggaagacct | gaaggttcag | 180 |
| catagtagct | acagacagag | ggcccggctg | ttgaaggacc | agctctccct | gggaaatgct | 240 |
| gcacttcaga | tcacagatgt | gaaattgcag | gatgcagggg | tgtaccgctg | catgatcagc | 300 |
| tatggtggtg | ccgactacaa | gcgaattact | gtgaaagtca | atgccccata | caacaaaatc | 360 |
| aaccaaagaa | ttttggttgt | ggatccagtc | acctctgaac | atgaactgac | atgtcaggct | 420 |
| gagggctacc | ccaaggccga | agtcatctgg | acaagcagtg | accatcaagt | cctgagtggt | 480 |
| aagaccacca | ccaccaattc | caagagagag | gagaagcttt | tcaatgtgac | cagcacactg | 540 |
| agaatcaaca | acaactaatg | agattttttc | tactgcactt | ttaggagatt | agatcctgag | 600 |
| gaaaaccata | cagctgaatt | ggtcatccca | gaactacctc | tggcacatcc | tccaaatgaa | 660 |
| aggactcact | tggtaattct | gggagccatc | ttattatgcc | ttggtgtagc | actgacattc | 720 |
| atcttccgtt | taagaaaagg | gagaatgatg | gatgtgaaaa | aatgtggcat | ccaagataca | 780 |
| aactcaaaga | agcaaagtga | tacacatttg | gaggagacgt | aa | | 822 |

<210> SEQ ID NO 5
<211> LENGTH: 3500
<212> TYPE: DNA
<213> ORGANISM: Artificial Sequence
<220> FEATURE:
<223> OTHER INFORMATION: expression vector pVAX10

<400> SEQUENCE: 5

| tgggcttttg | ctggcctttt | gctcacatgt | tcttgactct | tcgcgatgta | cgggccagat | 60 |
| atacgcgttg | acattgatta | ttgactagtt | attaatagta | atcaattacg | ggtcattag | 120 |
| ttcatagccc | atatatggag | ttccgcgtta | cataacttac | ggtaaatggc | ccgcctggct | 180 |

```
gaccgcccaa cgaccccgc ccattgacgt caataatgac gtatgttccc atagtaacgc    240
caatagggac tttccattga cgtcaatggg tggactattt acggtaaact gcccacttgg    300
cagtacatca agtgtatcat atgccaagta cgccccctat tgacgtcaat gacggtaaat    360
ggcccgcctg gcattatgcc cagtacatga ccttatggga cttcctact tggcagtaca    420 tctacgtatt agtcatcgct attaccatgg tgatgcggtt ttggcagtac atcaatgggc    480
gtggatagcg gtttgactca cggggatttc caagtctcca ccccattgac gtcaatggga    540
gtttgttttg gcaccaaaat caacgggact ttccaaaatg tcgtaacaac tccgccccat    600
tgacgcaaat gggcggtagg cgtgtacggt gggaggtcta tataagcaga gctctctggc    660
taactagaga acccactgct tactggctta tcgaaattaa tacgactcac tatagggaga    720
cccaagctgg ctagcctcga gtctagaggg cccgtttaaa cccgctgatc agcctcgact    780
gtgccttcta gttgccagcc atctgttgtt tgcccctccc ccgtgccttc cttgaccctg    840
gaaggtgcca ctcccactgt cctttcctaa taaaatgagg aaattgcatc gcattgtctg    900
agtaggtgtc attctattct ggggggtggg gtggggcagg acagcaaggg ggaggattgg    960
gaagacaata gcaggcatgc tggggatgcg gtgggctcta tggcttctac tgggcggttt   1020 tatgacagc aagcgaaccg gaattgccag ctggggcgcc ctctggtaag gttgggaagc   1080
cctgcaaagt aaactggatg gctttctcgc cgccaaggat ctgatggcgc aggggatcaa   1140
gctctgatca agagacagga tgaggatcgt ttcgcatgat tgaacaagat ggattgcacg   1200
caggttctcc ggccgcttgg gtggagaggc tattcggcta tgactgggca acagacaa   1260 tcggctgctc tgatgccgcc gtgttccggc tgtcagcgca ggggcgcccg gttcttttg   1320 tcaagaccga cctgtccggt gccctgaatg aactgcaaga cgaggcagcg cggctatcgt   1380
ggctggccac gacgggcgtt ccttgcgcag ctgtgctcga cgttgtcact gaagcgggaa   1440
gggactggct gctattgggc gaagtgccgg gcaggatct cctgtcatct caccttgctc   1500
ctgccgagaa agtatccatc atggctgatg caatgcggcg gctgcatacg cttgatccgg   1560
ctacctgccc attcgaccac caagcgaaac atcgcatcga gcgagcacgt actcggatgg   1620
aagccggtct tgtcgatcag gatgatctgg acgaagagca tcaggggctc gcgccagccg   1680
aactgttcgc caggctcaag gcgagcatgc ccgacggcga ggatctcgtc gtgacccatg   1740
gcgatgcctg cttgccgaat atcatggtgg aaaatggccg cttttctgga ttcatcgact   1800
gtggccggct gggtgtggcg gaccgctatc aggacatagc gttggctacc cgtgatattg   1860
ctgaagagct tggcggcgaa tgggctgacc gcttcctcgt gctttacggt atcgccgctc   1920
ccgattcgca gcgcatcgcc ttctatcgcc ttcttgacga gttcttctga attattaacg   1980
cttacaattt cctgatgcgg tattttctcc ttacgcatct gtgcggtatt tcacaccgca   2040
tacaggtggc acttttcggg gaaatgtgcg cggaacccct atttgtttat ttttctaaat   2100
acattcaaat atgtatccgc tcatgagaca ataaccctga taaatgcttc aataatagca   2160
cgtgctaaaa cttcattttt aatttaaaag gatctaggtg aagatccttt ttgataatct   2220
catgaccaaa atcccttaac gtgagttttc gttccactga gcgtcagacc cccatcagtg   2280
accaaacagg aaaaaaccgc ccttaacatg gcccgcttta tcagaagcca gacattaacg   2340
cttctggaga aactcaacga gctggacgcg gatgaacagg cagacatctg tgaatcgctt   2400
cacgaccacg ctgatgagct ttaccgcagc tgcctcgcgc gtttcggtga tgacggtgaa   2460
aacctctgac acatgcagct cccggagacg gtcacagctt gtctgtaagc ggatgccggg   2520
```

| | |
|---|---:|
| agcagacaag cccgtcaggg cgcgtcagcg ggtgttggcg ggtgtcgggg cgcagccatg | 2580 |
| acccagtcac gtagcgatag cggagtgtat actggcttaa ctatgcgcca tcagagcaga | 2640 |
| ttgtactgag agtgcaccat atgcggtgtg aaataccgca cagatgcgta aggagaaaat | 2700 |
| accgcatcag gcgctcttcc gcttcctcgc tcactgactc gctgcgctcg tcgttcggc | 2760 |
| tgcggcgagc ggtatcagct cactcaaagg cggtaatacg gttatccaca gaatcagggg | 2820 |
| ataacgcagg aaagaacatg tgagcaaaag gccagcaaaa ggccaggaac cgtaaaaagg | 2880 |
| ccgcgttgct ggcgtttttc cataggctcc gcccccctga cgagcatcac aaaaatcgac | 2940 |
| gctcaagtca gaggtggcga aacccgacag gactataaag ataccaggcg tttccccctg | 3000 |
| gaagctccct cgtgcgctct cctgttccga ccctgccgct taccggatac ctgtccgcct | 3060 |
| ttctcccttc gggaagcgtg gcgctttctc atagctcacg ctgtaggtat ctcagttcgg | 3120 |
| tgtaggtcgt tcgctccaag ctgggctgtg tgcacgaacc ccccgttcag cccgaccgct | 3180 |
| gcgccttatc cggtaactat cgtcttgagt ccaacccggt aagacacgac ttatcgccac | 3240 |
| tggcagcagc cactggtaac aggattagca gagcgaggta tgtaggcggt gctacagagt | 3300 |
| tcttgaagtg gtggcctaac tacggctaca ctagaaggac agtatttggt atctgcgctc | 3360 |
| tgctgaagcc agttaccttc ggaaaaagag ttggtagctc ttgatccggc aaacaaacca | 3420 |
| ccgctggtag cggtggtttt tttgtttgca agcagcagat tacgcgcaga aaaaaggat | 3480 |
| ctcaagaaga tcctttgatc | 3500 |

<210> SEQ ID NO 6
<211> LENGTH: 371
<212> TYPE: PRT
<213> ORGANISM: Homo sapiens

<400> SEQUENCE: 6

Met Gly Ser Asp Val Arg Asp Leu Asn Ala Leu Leu Pro Ala Val Pro
1               5                   10                  15

Ser Leu Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser

```
            195                 200                 205
Cys Thr Gly Ser Gln Ala Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
        260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys
    370

<210> SEQ ID NO 7
<211> LENGTH: 630
<212> TYPE: PRT
<213> ORGANISM: Homo sapiens

<400> SEQUENCE: 7

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Phe Leu Asn Pro
            115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190
```

```
Pro Gly Arg Phe Val Ala Glu Ser Ala Glu Val Leu Leu Pro Arg Leu
            195                 200                 205

Val Ser Cys Pro Gly Pro Leu Asp Gln Asp Gln Gln Glu Ala Ala Arg
210                 215                 220

Ala Ala Leu Gln Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
```

```
                610                 615                 620
Leu Ala Ser Thr Leu Ala
625                 630

<210> SEQ ID NO 8
<211> LENGTH: 702
<212> TYPE: PRT
<213> ORGANISM: Homo sapiens

<400> SEQUENCE: 8

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350
```

```
Thr Tyr Leu Trp Trp Val Asn Asn Gln Ser Leu Pro Val Ser Pro Arg
            355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
    435                 440                 445

Trp Leu Ile Asp Gly Asn Ile Gln Gln His Thr Gln Glu Leu Phe Ile
            450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
    515                 520                 525

Asn Thr Thr Tyr Leu Trp Trp Val Asn Gly Gln Ser Leu Pro Val Ser
            530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
    595                 600                 605

Ala Asn Leu Asn Leu Ser Cys His Ser Ala Ser Asn Pro Ser Pro Gln
            610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
    675                 680                 685

Val Gly Ile Met Ile Gly Val Leu Val Gly Val Ala Leu Ile
            690                 695                 700

<210> SEQ ID NO 9
<211> LENGTH: 561
<212> TYPE: PRT
<213> ORGANISM: Cytomegalovirus

<400> SEQUENCE: 9

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30
```

```
Pro Val Leu Pro His Glu Thr Arg Leu Leu Gln Thr Gly Ile His Val
         35                  40                  45

Arg Val Ser Gln Pro Ser Leu Ile Leu Val Ser Gln Tyr Thr Pro Asp
 50                  55                  60

Ser Thr Pro Cys His Arg Gly Asp Asn Gln Leu Gln Val Gln His Thr
 65                  70                  75                  80

Tyr Phe Thr Gly Ser Glu Val Glu Asn Val Ser Val Asn Val His Asn
                 85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
            195                 200                 205

Glu Asn Thr Arg Ala Thr Lys Met Gln Val Ile Gly Asp Gln Tyr Val
        210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
                260                 265                 270

Thr Val Leu Cys Pro Lys Asn Met Ile Ile Lys Pro Gly Lys Ile Ser
            275                 280                 285

His Ile Met Leu Asp Val Ala Phe Thr Ser His Glu His Phe Gly Leu
        290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
370                 375                 380

Trp Asp Arg His Asp Glu Gly Ala Ala Gln Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Lys Arg Lys Ser Ala Ser Ser Ala Thr Ala Cys Thr Ala
        435                 440                 445
```

-continued

```
Gly Val Met Thr Arg Gly Arg Leu Lys Ala Glu Ser Thr Val Ala Pro
            450                 455                 460
Glu Glu Asp Thr Asp Glu Asp Ser Asp Asn Glu Ile His Asn Pro Ala
465                 470                 475                 480
Val Phe Thr Trp Pro Pro Trp Gln Ala Gly Ile Leu Ala Arg Asn Leu
                485                 490                 495
Val Pro Met Val Ala Thr Val Gln Gly Gln Asn Leu Lys Tyr Gln Glu
                500                 505                 510
Phe Phe Trp Asp Ala Asn Asp Ile Tyr Arg Ile Phe Ala Glu Leu Glu
            515                 520                 525
Gly Val Trp Gln Pro Ala Ala Gln Pro Lys Arg Arg Arg His Arg Gln
        530                 535                 540
Asp Ala Leu Pro Gly Pro Cys Ile Ala Ser Thr Pro Lys Lys His Arg
545                 550                 555                 560
Gly

<210> SEQ ID NO 10
<211> LENGTH: 561
<212> TYPE: PRT
<213> ORGANISM: Cytomegalovirus

<400> SEQUENCE: 10

Met Glu Ser Arg Gly Arg Arg Cys Pro Glu Met Ile Ser Val Leu Gly
1               5                   10                  15
Pro Ile Ser Gly His Val Leu Lys Ala Val Phe Ser Arg Gly Asp Thr
                20                  25                  30
Pro Val Leu Pro His Glu Thr Arg Leu Leu Gln Thr Gly Ile His Val
            35                  40                  45
Arg Val Ser Gln Pro Ser Leu Ile Leu Val Ser Gln Tyr Thr Pro Asp
        50                  55                  60
Ser Thr Pro Cys His Arg Gly Asp Asn Gln Leu Gln Val Gln His Thr
65                  70                  75                  80
Tyr Phe Thr Gly Ser Glu Val Glu Asn Val Ser Val Asn Val His Asn
                85                  90                  95
Pro Thr Gly Arg Ser Ile Cys Pro Ser Gln Glu Pro Met Ser Ile Tyr
                100                 105                 110
Val Tyr Ala Leu Pro Leu Lys Met Leu Asn Ile Pro Ser Ile Asn Val
            115                 120                 125
His His Tyr Pro Ser Ala Ala Glu Arg Lys His Arg His Leu Pro Val
130                 135                 140
Ala Asp Ala Val Ile His Ala Ser Gly Lys Gln Met Trp Gln Ala Arg
145                 150                 155                 160
Leu Thr Val Ser Gly Leu Ala Trp Thr Arg Gln Gln Asn Gln Trp Lys
                165                 170                 175
Glu Pro Asp Val Tyr Tyr Thr Ser Ala Phe Val Phe Pro Thr Lys Asp
            180                 185                 190
Val Ala Leu Arg His Val Val Cys Ala His Glu Leu Val Cys Ser Met
        195                 200                 205
Glu Asn Thr Arg Ala Thr Lys Met Gln Val Ile Gly Asp Gln Tyr Val
    210                 215                 220
Lys Val Tyr Leu Glu Ser Phe Cys Glu Asp Val Pro Ser Gly Lys Leu
225                 230                 235                 240
Phe Met His Val Thr Leu Gly Ser Asp Val Glu Glu Asp Leu Thr Met
                245                 250                 255
```

```
Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
            420                 425                 430

Ala Gly Arg Asn Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 11
<211> LENGTH: 536
<212> TYPE: PRT
<213> ORGANISM: Cytomegalovirus

<400> SEQUENCE: 11

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60
```

```
Ser Thr Pro Cys His Arg Gly Asp Asn Gln Leu Gln Val Gln His Thr
 65                  70                  75                  80

Tyr Phe Thr Gly Ser Glu Val Glu Asn Val Ser Val Asn Val His Asn
                 85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Asn Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
```

```
                        485                 490                 495
Val Pro Met Val Ala Thr Val Gln Gly Gln Asn Leu Lys Tyr Gln Glu
                500                 505                 510

Phe Phe Trp Asp Ala Asn Asp Ile Tyr Arg Ile Phe Ala Glu Leu Glu
            515                 520                 525

Gly Val Trp Gln Pro Ala Ala Gln
        530                 535

<210> SEQ ID NO 12
<211> LENGTH: 1355
<212> TYPE: PRT
<213> ORGANISM: Homo sapiens

<400> SEQUENCE: 12

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320
```

-continued

```
Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Gly Ile Val Leu Lys Asp Gly Asn Arg Asn
705                 710                 715                 720

Leu Thr Ile Arg Arg Val Arg Lys Glu Asp Glu Gly Leu Tyr Thr Cys
                725                 730                 735

Gln Ala Cys Ser Val Leu Gly Cys Ala Lys Val Glu Ala Phe Phe Ile
```

```
            740                 745                 750
Ile Glu Gly Ala Gln Glu Lys Thr Asn Leu Glu Ile Ile Leu Val
            755                 760                 765

Gly Thr Ala Val Ile Ala Met Phe Phe Trp Leu Leu Leu Val Ile Ile
            770                 775                 780

Leu Arg Thr Val Lys Arg Ala Asn Gly Gly Glu Leu Lys Thr Gly Tyr
785                 790                 795                 800

Leu Ser Ile Val Met Asp Pro Asp Glu Leu Pro Leu Asp Glu His Cys
                    805                 810                 815

Glu Arg Leu Pro Tyr Asp Ala Ser Lys Trp Glu Phe Pro Arg Asp Arg
                    820                 825                 830

Leu Lys Leu Gly Lys Pro Leu Gly Arg Gly Ala Phe Gly Gln Val Ile
                835                 840                 845

Glu Ala Asp Ala Phe Gly Ile Asp Lys Thr Ala Thr Cys Arg Thr Val
            850                 855                 860

Ala Val Lys Met Leu Lys Glu Gly Ala Thr His Ser Glu His Arg Ala
865                 870                 875                 880

Leu Met Ser Glu Leu Lys Ile Leu Ile His Ile Gly His His Leu Asn
                    885                 890                 895

Val Val Asn Leu Leu Gly Ala Cys Thr Lys Pro Gly Gly Pro Leu Met
                900                 905                 910

Val Ile Val Glu Phe Cys Lys Phe Gly Asn Leu Ser Thr Tyr Leu Arg
                915                 920                 925

Ser Lys Arg Asn Glu Phe Val Pro Tyr Lys Thr Lys Gly Ala Arg Phe
            930                 935                 940

Arg Gln Gly Lys Asp Tyr Val Gly Ala Ile Pro Val Asp Leu Lys Arg
945                 950                 955                 960

Arg Leu Asp Ser Ile Thr Ser Ser Gln Ser Ala Ser Ser Gly Phe
                    965                 970                 975

Val Glu Glu Lys Ser Leu Ser Asp Val Glu Glu Glu Ala Pro Glu
                980                 985                 990

Asp Leu Tyr Lys Asp Phe Leu Thr Leu Glu His Leu Ile Cys Tyr Ser
                    995                 1000                1005

Phe Gln Val Ala Lys Gly Met Glu Phe Leu Ala Ser Arg Lys Cys Ile
            1010                1015                1020

His Arg Asp Leu Ala Ala Arg Asn Ile Leu Leu Ser Glu Lys Asn Val
1025                1030                1035                1040

Val Lys Ile Cys Asp Phe Gly Leu Ala Arg Asp Ile Tyr Lys Asp Pro
                    1045                1050                1055

Asp Tyr Val Arg Lys Gly Asp Ala Arg Leu Pro Leu Lys Trp Met Ala
                1060                1065                1070

Pro Glu Thr Ile Phe Asp Arg Val Tyr Thr Ile Gln Ser Asp Val Trp
                1075                1080                1085

Ser Phe Gly Val Leu Leu Trp Glu Ile Phe Ser Leu Gly Ala Ser Pro
            1090                1095                1100

Tyr Pro Gly Val Lys Ile Asp Glu Glu Phe Cys Arg Arg Leu Lys Glu
1105                1110                1115                1120

Gly Thr Arg Met Arg Ala Pro Asp Tyr Thr Thr Pro Glu Met Tyr Gln
                    1125                1130                1135

Thr Met Leu Asp Cys Trp His Gly Glu Pro Ser Gln Arg Pro Thr Phe
                1140                1145                1150

Ser Glu Leu Val Glu His Leu Gly Asn Leu Leu Gln Ala Asn Ala Gln
                1155                1160                1165
```

Gln Asp Gly Lys Asp Tyr Ile Val Leu Pro Ile Ser Glu Thr Leu Ser
    1170                1175                1180

Met Glu Glu Asp Ser Gly Leu Ser Leu Pro Thr Ser Pro Val Ser Cys
1185                1190                1195                1200

Met Glu Glu Glu Val Cys Asp Pro Lys Phe His Tyr Asp Asn Thr
                1205                1210                1215

Ala Gly Ile Ser Gln Tyr Leu Gln Asn Ser Lys Arg Lys Ser Arg Pro
                1220                1225                1230

Val Ser Val Lys Thr Phe Glu Asp Ile Pro Leu Glu Glu Pro Glu Val
        1235                1240                1245

Lys Val Ile Pro Asp Asp Asn Gln Thr Asp Ser Gly Met Val Leu Ala
        1250                1255                1260

Ser Glu Glu Leu Lys Thr Leu Glu Asp Arg Thr Lys Leu Ser Pro Ser
1265                1270                1275                1280

Phe Gly Gly Met Val Pro Ser Lys Ser Arg Glu Ser Val Ala Ser Glu
                1285                1290                1295

Gly Ser Asn Gln Thr Ser Gly Tyr Gln Ser Gly Tyr His Ser Asp Asp
                1300                1305                1310

Thr Asp Thr Thr Val Tyr Ser Ser Glu Glu Ala Glu Leu Leu Lys Leu
            1315                1320                1325

Ile Glu Ile Gly Val Gln Thr Gly Ser Thr Ala Gln Ile Leu Gln Pro
            1330                1335                1340

Asp Ser Gly Thr Thr Leu Ser Ser Pro Pro Val
1345                1350                1355

<210> SEQ ID NO 13
<211> LENGTH: 238
<212> TYPE: PRT
<213> ORGANISM: Homo sapiens

<400> SEQUENCE: 13

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn

```
                180                 185                 190
Val Thr Ser Thr Leu Arg Ile Asn Thr Thr Asn Glu Ile Phe Tyr
            195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg
225                 230                 235

<210> SEQ ID NO 14
<211> LENGTH: 717
<212> TYPE: DNA
<213> ORGANISM: Homo sapiens

<400> SEQUENCE: 14
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca gcgaattact gtgaaagtc aatgccccat acaacaaaat caaccaaaga     420
attttggttg tggatccagt cacctctgaa catgaactga catgtcaggc tgagggctac     480
cccaaggccg aagtcatctg gacaagcagt gaccatcaag tcctgagtgg taagaccacc     540
accaccaatt ccaagagaga ggagaagctt ttcaatgtga ccagcacact gagaatcaac     600
acaacaacta atgagatttt ctactgcact tttaggagat tagatcctga ggaaaaccat     660
acagctgaat tggtcatccc agaactacct ctggcacatc ctccaaatga aggtaa        717

<210> SEQ ID NO 15
<211> LENGTH: 239
<212> TYPE: PRT
<213> ORGANISM: Mus musculus

<400> SEQUENCE: 15

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
```

```
                145                 150                 155                 160
Glu Ala Glu Val Ile Trp Thr Asn Ser Asp His Gln Pro Val Ser Gly
                165                 170                 175
Lys Arg Ser Val Thr Thr Ser Arg Thr Glu Gly Met Leu Leu Asn Val
                180                 185                 190
Thr Ser Ser Leu Arg Val Asn Ala Thr Ala Asn Asp Val Phe Tyr Cys
                195                 200                 205
Thr Phe Trp Arg Ser Gln Pro Gly Gln Asn His Thr Ala Glu Leu Ile
            210                 215                 220
Ile Pro Glu Leu Pro Ala Thr His Pro Pro Gln Asn Arg Thr His
225                 230                 235

<210> SEQ ID NO 16
<211> LENGTH: 720
<212> TYPE: DNA
<213> ORGANISM: Mus musculus

<400> SEQUENCE: 16
atgaggatat ttgctggcat tatattcaca gcctgctgtc acttgctacg ggcgtttact      60
atcacggctc caaaggactt gtacgtggtg gagtatggca gcaacgtcac gatggagtgc     120
agattccctg tagaacggga gctggacctg cttgcgttag tggtgtactg ggaaaaggaa     180
gatgagcaag tgattcagtt tgtggcagga gaggaggacc ttaagcctca gcacagcaac     240 ttcagggga gagcctcgct gccaaaggac cagcttttga agggaaatgc tgcccttcag     300
atcacagacg tcaagctgca ggacgcaggc gtttactgct gcataatcag ctacggtggt     360
gcggactaca gcgaatcac gctgaaagtc aatgccccat accgcaaaat caaccagaga     420
atttccgtgg atccagccac ttctgagcat gaactaatat gtcaggccga gggttatcca     480
gaagctgagg taatctggac aaacagtgac caccaacccg tgagtgggaa gagaagtgtc     540
accacttccc ggacagaggg gatgcttctc aatgtgacca gcagtctgag ggtcaacgcc     600
acagcgaatg atgttttcta ctgtacgttt tggagatcac agccagggca aaaccacaca     660
gcggagctga tcatcccaga actgcctgca acacatcctc cacagaacag gactcactaa     720

<210> SEQ ID NO 17
<211> LENGTH: 873
<212> TYPE: DNA
<213> ORGANISM: Mus musculus

<400> SEQUENCE: 17
atgaggatat ttgctggcat tatattcaca gcctgctgtc acttgctacg ggcgtttact      60
atcacggctc caaaggactt gtacgtggtg gagtatggca gcaacgtcac gatggagtgc     120
agattccctg tagaacggga gctggacctg cttgcgttag tggtgtactg ggaaaaggaa     180
gatgagcaag tgattcagtt tgtggcagga gaggaggacc ttaagcctca gcacagcaac     240 ttcagggga gagcctcgct gccaaaggac cagcttttga agggaaatgc tgcccttcag     300
atcacagacg tcaagctgca ggacgcaggc gtttactgct gcataatcag ctacggtggt     360
gcggactaca gcgaatcac gctgaaagtc aatgccccat accgcaaaat caaccagaga     420
atttccgtgg atccagccac ttctgagcat gaactaatat gtcaggccga gggttatcca     480
gaagctgagg taatctggac aaacagtgac caccaacccg tgagtgggaa gagaagtgtc     540
accacttccc ggacagaggg gatgcttctc aatgtgacca gcagtctgag ggtcaacgcc     600
acagcgaatg atgttttcta ctgtacgttt tggagatcac agccagggca aaaccacaca     660
```

```
gcggagctga tcatcccaga actgcctgca acacatcctc cacagaacag gactcactgg    720
gtgcttctgg gatccatcct gttgttcctc attgtagtgt ccacggtcct cctcttcttg    780
agaaaacaag tgagaatgct agatgtggag aaatgtggcg ttgaagatac aagctcaaaa    840
aaccgaaatg atacacaatt cgaggagacg taa                                 873

<210> SEQ ID NO 18
<211> LENGTH: 822
<212> TYPE: DNA
<213> ORGANISM: Mus musculus

<400> SEQUENCE: 18
atgtttacta tcacggctcc aaaggacttg tacgtggtgg agtatggcag caacgtcacg     60
atggagtgca gattccctgt agaacggag ctggacctgc ttgcgttagt ggtgtactgg    120
gaaaaggaag atgagcaagt gattcagttt gtggcaggag aggaggacct taagcctcag    180
cacagcaact tcaggggag agcctcgctg ccaaaggacc agcttttgaa gggaaatgct    240
gcccttcaga tcacagacgt caagctgcag gacgcaggcg tttactgctg cataatcagc    300
tacggtggtg cggactacaa gcgaatcacg ctgaaagtca atgccccata ccgcaaaatc    360
aaccagagaa tttccgtgga tccagccact tctgagcatg aactaatatg tcaggccgag    420
ggttatccag aagctgaggt aatctggaca aacagtgacc accaacccgt gagtgggaag    480
agaagtgtca ccacttcccg gacagaggg atgcttctca atgtgaccag cagtctgagg    540
gtcaacgcca cagcgaatga tgtttttctac tgtacgtttt ggagatcaca gccagggcaa    600
aaccacacag cggagctgat catcccagaa ctgcctgcaa cacatcctcc acagaacagg    660
actcactggg tgcttctggg atccatcctg ttgttcctca ttgtagtgtc cacggtcctc    720
ctcttcttga gaaaacaagt gagaatgcta gatgtggaga aatgtggcgt tgaagataca    780
agctcaaaaa accgaaatga tacacaattc gaggagacgt aa                       822

<210> SEQ ID NO 19
<211> LENGTH: 18
<212> TYPE: PRT
<213> ORGANISM: Homo sapiens
<220> FEATURE:
<223> OTHER INFORMATION: Signaling peptide of human PD-L1

<400> SEQUENCE: 19

Met Arg Ile Phe Ala Val Phe Ile Phe Met Thr Tyr Trp His Leu Leu
1               5                   10                  15

Asn Ala
```

PD-L1 TARGETING DNA VACCINE FOR CANCER IMMUNOTHERAPY

CROSS-REFERENCE TO RELATED APPLICATIONS

This application is a national phase entry pursuant to 35 U.S.C. § 371 of International Application No. PCT/EP2018/056721, filed Mar. 16, 2018, which claims priority from European Application Nos. EP 17161666.7, filed Mar. 17, 2017, and EP 17188941.3, filed Sep. 1, 2017, the entire contents of which are incorporated by reference herein for all purposes.

FIELD OF THE INVENTION

The present invention relates to an attenuated strain of *Salmonella* comprising at least one copy of a DNA molecule comprising an expression cassette encoding PD-L1. In particular, the present invention relates to said attenuated strain of *Salmonella* for use in the treatment of cancer.

BACKGROUND OF THE INVENTION

An important characteristic of the immune system is its ability to discriminate between "self" and "foreign." To this end, it uses "checkpoint"—molecules on certain immune cells that need to be activated (or inactivated) to start an immune response.

Principally, the immune system has the capacity to recognize and destroy neoplastic cells. T-cells appear to be major effectors in anti-cancer immunity. However, many tumors develop mechanisms to evade the immune system to enhance their survival. Immune regulatory proteins such as checkpoint proteins and their ligands play vital roles in immune suppression and tolerance induction of anti-cancer immune responses.

Programmed cell death 1 (PD-1) is expressed on the surface of T-cells and transmits inhibitory signals that maintain T-cell functional silence against cognate antigens. Its ligand PD-L1 is normally expressed on antigen-presenting cells, placental cells and non-hematopoietic cells in inflammatory microenvironments. PD-L1 has been reported to be expressed on immunosuppressive myeloid-derived suppressor cells (MDSC). In addition, PD-L1 is extensively expressed on the surface of various types of cancer cells, which use the PD-1/PD-L1 signaling axis to escape the host immune system. Expression of PD-L1 by cancer cells was shown to correlate with disease stage and poor patient prognosis.

The potential of targeting the PD-L1/PD-1 signaling pathway has been demonstrated in clinical trials evaluating several monoclonal anti-PD-1 and anti-PD-L1 antibodies, which function by inhibiting binding of PD-L1 to PD-1. These antibodies are designed to unleash or enhance pre-existing anti-cancer immune responses. Different agents are currently investigated in clinical trials in patients like Opdivo (nivolumab, an anti-PD-1 antibody) in various solid tumours and hematological malignancies, pembrolizumab (Keytruda, an anti-PD-1 antibody) in various solid tumours and hematological malignancies, CT-011 (anti-PD-1) in conjunction with a dendritic cell vaccine in AML following chemotherapy-induced remission, and lirilumab (anti-KIR) combined with rituximab in relapsed, refractory or high-risk untreated patients with CLL. Furthermore, anti-PD-L1 monoclonal antibodies including atezolizumab, avelumab or durvalumab are in advanced clinical development in various cancer indications.

Only recently, the existence of PD-L1-specific T-cells has been described.

WO 2013/056716 discloses a HLA (human leukocyte antigen)-A2-restricted PD-L1 peptide vaccine.

WO 2014/005683 discloses an attenuated mutant strain of *Salmonella* comprising a recombinant DNA molecule encoding a VEGF receptor protein for use in cancer immunotherapy, particularly for use in the treatment of pancreatic cancer.

WO 2016/202459 discloses a cancer therapy approach comprising the combined administration of an attenuated mutant strain of *Salmonella* comprising a recombinant DNA molecule encoding a VEGF receptor protein and a checkpoint inhibitor antibody.

To the inventor's knowledge, no bacterial DNA vaccine targeting PD-L1 with the aim to induce PD-L1-specific cytotoxic immune cells that directly target PD-L1 positive tumor cells has been reported. Furthermore, no oral cancer vaccine targeting PD-L1 has been described.

OBJECTS OF THE INVENTION

In view of the prior art, it is an object of the present invention to provide a novel safe and efficient PD-L1 targeting cancer treatment. Such a novel therapy approach would offer major advantages for improving the treatment options for cancer patients.

SUMMARY OF THE INVENTION

The present invention is based on the surprising finding that a *Salmonella*-based DNA delivery vehicle carrying a recombinant DNA construct encoding either full length PD-L1 or truncated PD-L1 comprising the extracellular domain of PD-L1 exhibits high antitumor efficacy in C57BL/6 mice bearing disseminated syngeneic FBL-3 erythroleukemia.

Thus, in a first aspect, the present invention relates to an attenuated strain of *Salmonella* comprising at least one copy of a DNA molecule comprising an expression cassette encoding PD-L1.

In particular embodiments, the attenuated strain of *Salmonella* is of the species *Salmonella enterica*. Particularly, the attenuated strain of *Salmonella* is *Salmonella typhi* Ty21a.

In particular embodiments, the expression cassette is a eukaryotic expression cassette. Particularly, the expression cassette comprises a CMV promoter.

In particular embodiments, PD-L1 is selected from the group consisting of full length PD-L1 and a truncated PD-L1 comprising the extracellular domain of PD-L1. A truncated PD-L1 may comprise an amino acid sequence of amino acids 19 to 238 of of SEQ ID NO 13, the amino acid sequence of SEQ ID NO 13, the amino acid sequence of SEQ ID NO 2 or may comprise an amino acid sequence that shares at least 80% sequence identity with amino acids 19 to 238 of SEQ ID NO 13, with SEQ ID NO 13 or with SEQ ID NO 2. In particular embodiments the PD-L1 is selected from the group consisting of PD-L1 having the amino acid sequence as found in SEQ ID NO 1 and a protein that shares at least 80% sequence identity therewith. In particular other embodiments, PD-L1 is selected from the group consisting of PD-L1 having the amino acid sequence as found in SEQ ID NO 2 and a protein that shares at least 80% sequence identity therewith. In particular other embodiments, PD-L1 is selected from the group consisting of PD-L1 having the amino acid sequence as found in SEQ ID NO 13 and a protein that shares at least 80% sequence identity therewith. In particular other embodiments, PD-L1 is selected from the group consisting of PD-L1 having the amino acid sequence of amino acids 19 to 238 of SEQ ID NO 13 and a protein that shares at least 80% sequence identity therewith. Particularly, PD-L1 has the amino acid sequence as found in SEQ ID NO 1, SEQ ID NO 2 or SEQ ID NO 13, preferably PD-L1 comprises the amino acid sequence of amino acids 19 to 238 of SEQ ID NO 13. In one embodiment PD-L1 comprises at least the extracellular domain with or without the signaling peptide.

In particular embodiments, PD-L1 is encoded by the nucleic acid sequence as found in SEQ ID NO 3, SEQ ID NO 4 or SEQ ID NO 14.

In particular embodiments, the DNA molecule further comprises the kanamycin antibiotic resistance gene, the pMB1 ori and a CMV promoter.

Particularly, the DNA molecule further comprises the DNA sequence as found in SEQ ID NO 5.

In a second aspect, the present invention relates to the attenuated strain of *Salmonella* according to the present invention for use as a medicament.

In particular embodiments, the attenuated strain of *Salmonella* is for use in the treatment of cancer.

In particular embodiments, the attenuated strain of *Salmonella* is for use in cancer immunotherapy.

In particular embodiments, the treatment of cancer further comprises chemotherapy, radiotherapy or biological cancer therapy. Particularly, the attenuated strain of *Salmonella* is administered before, during and/or after the chemotherapy or the radiotherapy treatment or the biological cancer therapy. More particularly, the attenuated strain of *Salmonella* is administered before and during the chemotherapy or the radiotherapy treatment or the biological cancer therapy.

In particular embodiments, the biological cancer therapy comprises administration of at least one further DNA vaccine encoding a tumor antigen and/or a tumor stroma antigen. In particular embodiments, the at least one further DNA vaccine is selected from at least one attenuated strain of *Salmonella* comprising at least one copy of a DNA molecule comprising an expression cassette encoding a tumor antigen and/or a tumor stroma antigen. This includes at least one further DNA vaccine comprising at least one copy of a DNA molecule comprising an expression cassette encoding a tumor antigen and/or at least one further DNA vaccine comprising at least one copy of a DNA molecule comprising an expression cassette encoding a tumor stroma antigen. Particularly, said at least one further attenuated strain of *Salmonella* is *Salmonella typhi* Ty21a comprising a eukaryotic expression cassette.

In one embodiment said tumor antigen is selected from Wilms' Tumor Protein (WT1), Mesothelin (MSLN), carcinoembryonic antigen (CEA) and CMV pp65. In particular embodiments, said tumor antigen encoded by said at least one further DNA vaccine is selected from the group consisting of Wilms' Tumor Protein (WT1) having the amino acid sequence as found in SEQ ID NO 6 and a protein that shares at least about 80% sequence identity therewith, Mesothelin (MSLN) having the amino acid sequence as found in SEQ ID NO 7 and a protein that shares at least about 80% sequence identity therewith, CEA having the amino acid sequence as found in SEQ ID NO 8 and a protein that shares at least about 80% sequence identity therewith, CMV pp65 having the amino acid sequence as found in SEQ ID NO 9 and a protein that shares at least about 80% sequence identity therewith, CMV pp65 having the amino acid sequence as found in SEQ ID NO 10 and a protein that shares at least about 80% sequence identity therewith, and CMV pp65 having the amino acid sequence as found in SEQ ID NO 11 and a protein that shares at least about 80% sequence identity therewith. Particularly, Wilms' Tumor Protein (WT1) has the amino acid sequence as found in SEQ ID NO 6, Mesothelin (MSLN) has the amino acid sequence as found in SEQ ID NO 7, CEA has the amino acid sequence as found in SEQ ID NO 8, and CMV pp65 has the amino acid sequence as found in SEQ ID NO 9, SEQ ID NO 10 or SEQ ID NO 11. In one embodiment said tumor stroma antigen is VEGFR-2 or fibroblast activation protein (FAP), preferably VEGFR-2. Particularly, said tumor stroma antigen encoded by said at least one further DNA vaccine is selected from the group consisting of VEGFR-2 having the amino acid sequence as found in SEQ ID NO 12 and a protein that shares at least about 80% sequence identity therewith and human fibroblast activation protein (FAP). Particularly, VEGFR-2 has the amino acid sequence as found in SEQ ID NO 12.

In particular embodiments, the attenuated strain of *Salmonella* is administered orally.

In particular embodiments, the cancer is selected from lymphoma, leukemia, myeloma, lung cancer, in particular non-small cell lung cancer (NSCLC), melanoma, renal cell cancer, ovarian cancer, glioblastoma, merkel cell carcinoma, bladder cancer, head and neck cancer, colorectal cancer, esophagial cancer, cervical cancer, gastric cancer, hepatocellular cancer, prostate cancer, breast cancer, pancreatic cancer, and thyroid cancer.

In particular embodiments, the single dose of the attenuated strain of *Salmonella* comprises from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In particular embodiments, the attenuated strain of *Salmonella* is for use in individualized cancer immunotherapy comprising the step of assessing the PD-L1 expression pattern and/or the pre-immune response against PD-L1 of a patient.

DETAILED DESCRIPTION OF THE INVENTION

In a first aspect, the present invention relates to an attenuated strain of *Salmonella* comprising at least one copy of a DNA molecule comprising an expression cassette encoding PD-L1.

The live attenuated *Salmonella* strain according to the present invention stably carries a recombinant DNA molecule encoding PD-L1. It can be used as a vehicle for the oral delivery of this recombinant DNA molecule.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuation can be accomplished by deletion of various genes, including virulence, regulatory, and metabolic genes. Attenuated bacteria may be found naturally or they may be produced artificially in the laboratory, for example by adaptation to a new medium or cell culture or they may be produced by recombinant DNA technology. Administration of about $10^{11}$ CFU of the attenuated strain of *Salmonella* according to the present invention preferably causes *Salmonellosis* in less than 5%, more preferably less than 1%, most preferably less than 1‰ of subjects.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

The DNA molecule comprising an expression cassette encoding PD-L1 is suitably a recombinant DNA molecule, i.e. an engineered DNA construct, preferably composed of DNA pieces of different origin. The DNA molecule can be a linear nucleic acid, or preferably, a circular DNA plasmid generated by introducing an open reading frame encoding PD-L1 into an expression vector plasmid. Suitable expression vector plasmids are for instance, without being limited thereto, pVAX1™ (Invitrogen, San Diego, Calif.) or pcDNA™3.1 (Invitrogen, San Diego, Calif.), or expression vector plasmids derived thereof. The expression vector plasmids may contain a high copy origin, such as a pUC ori, or a low copy origin, such as a pMB1 ori.

In the context of the present invention, the term "expression cassette" refers to a nucleic acid unit comprising at least one open reading frame (ORF) under the control of regulatory sequences controlling its expression. Expression cassettes can preferably mediate transcription of the included open reading frame encoding a recombinant protein, such as PD-L1, in a target cell. Expression cassettes typically comprise a promoter, at least one open reading frame and a transcription termination signal.

In particular embodiments, the attenuated strain of *Salmonella* is of the species *Salmonella enterica*. Attenuated derivatives of *Salmonella enterica* are attractive vehicles for the delivery of heterologous antigens to the mammalian immune system, since *S. enterica* strains can potentially be delivered via mucosal routes of immunization, i.e. orally or nasally, which offers advantages of simplicity and safety compared to parenteral administration. Furthermore, *Salmonella* strains elicit strong humoral and cellular immune responses at the level of both systemic and mucosal compartments. Batch preparation costs are low and formulations of live bacterial vaccines are highly stable. Attenuation can be accomplished by deletion of various genes, including virulence, regulatory, and metabolic genes.

Several *Salmonella typhimurium* strains attenuated by aro mutations have been shown to be safe and effective delivery vehicles for heterologous antigens in animal models.

In particular embodiments, the attenuated strain of *Salmonella* is *Salmonella typhi* Ty21a. The live, attenuated *S. typhi* Ty21a strain is the active component of Typhoral L®, also known as Vivotif® (manufactured by Berna Biotech Ltd., a Crucell Company, Switzerland). It is currently the only licensed live oral vaccine against typhoid fever. This vaccine has been extensively tested and has proved to be safe regarding patient toxicity as well as transmission to third parties (Wahdan et al., J. Infectious Diseases 1982, 145:292-295). The vaccine is licensed in more than 40 countries and has been used in millions of individuals including thousands of children for prophylactic vaccination against typhoid fever. It has an unparalleled safety track record. There is no data available indicating that *S. typhi* Ty21a is able to enter the bloodstream systemically. The live attenuated *Salmonella typhi* Ty21a vaccine strain thus allows specific targeting of the immune system in the gut, while being safe and well-tolerated. The Marketing Authorization number of Typhoral L® is PL 15747/0001 dated 16 Dec. 1996. One dose of vaccine contains at least $2 \times 10^9$ viable *S. typhi* Ty21a colony forming units and at least $5 \times 10^9$ non-viable *S. typhi* Ty21a cells.

This well-tolerated, live oral vaccine against typhoid fever was derived by chemical mutagenesis of the wild-type virulent bacterial isolate *S. typhi* Ty2 and harbors a loss-of-function mutation in the galE gene resulting in its inability to metabolize galactose. The attenuated bacterial strain is also not able to reduce sulfate to sulfide which differentiates it from the wild-type *Salmonella typhi* Ty2 strain. With regard to its serological characteristics, the *Salmonella typhi* Ty21a strain contains the O9-antigen which is a polysaccharide of the outer membrane of the bacteria and lacks the O5-antigen which is in turn a characteristic component of *Salmonella typhimurium*. This serological characteristic supports the rationale for including the respective test in a panel of identity tests for batch release.

In particular embodiments, the expression cassette is a eukaryotic expression cassette. Particularly, the expression cassette comprises a CMV promoter. In the context of the present invention, the term "eukaryotic expression cassette" refers to an expression cassette which allows for expression of the open reading frame in a eukaryotic cell. It has been shown that the amount of heterologous antigen required to induce an adequate immune response may be toxic for the bacterium and may result in cell death, over-attenuation or loss of expression of the heterologous antigen. Using a eukaryotic expression cassette that is not expressed in the bacterial vector but only in the target cell may overcome this toxicity problem and the protein expressed typically exhibits a eukaryotic glycosylation pattern.

A eukaryotic expression cassette comprises regulatory sequences that are able to control the expression of an open reading frame in a eukaryotic cell, preferably a promoter and a polyadenylation signal. Promoters and polyadenylation signals included in the recombinant DNA molecules comprised by the attenuated strain of *Salmonella* of the present invention are preferably selected to be functional within the cells of the subject to be immunized. Examples of suitable promoters, especially for the production of a DNA vaccine for humans, include but are not limited to promoters from Cytomegalovirus (CMV), such as the strong CMV immediate early promoter, Simian Virus 40 (SV40), Mouse Mammary Tumor Virus (MMTV), Human Immunodeficiency Virus (HIV), such as the HIV Long Terminal Repeat (LTR) promoter, Moloney virus, Epstein Barr Virus (EBV), and from Rous Sarcoma Virus (RSV), the synthetic CAG promoter composed of the CMV early enhancer element, the promoter, the first exon and the first intron of chicken beta-actin gene and the splice acceptor of the rabbit beta globin gene, as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH)

polyadenylation site, SV40 polyadenylation signals and LTR polyadenylation signals. In a particular embodiment, the eukaryotic expression cassette included in the recombinant DNA molecule comprised by the attenuated strain of *Salmonella* of the present invention comprises the BGH polyadenylation site.

In addition to the regulatory elements required for heterologous gene expression, like a promoter and a polyadenylation signal, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In one embodiment, PD-L1 is selected from the group consisting of full length PD-L1 and a truncated PD-L1 comprising the extracellular domain of PD-L1. A truncated PD-L1 may comprise an amino acid sequence of amino acids 19 to 238 of of SEQ ID NO 13, the amino acid sequence of SEQ ID NO 13, the amino acid sequence of SEQ ID NO 2 or may comprise an amino acid sequence that shares at least 80% sequence identity with amino acids 19 to 238 of SEQ ID NO 13, with SEQ ID NO 13 or with SEQ ID NO 2. In particular embodiments, PD-L1 is selected from the group consisting of PD-L1 having the amino acid sequence as found in SEQ ID NO 1 and a protein that shares at least 80% sequence identity therewith. In particular other embodiments, PD-L1 is selected from the group consisting of PD-L1 having the amino acid sequence as found in SEQ ID NO 2 and a protein that shares at least 80% sequence identity therewith. In yet other particular embodiments, PD-L1 is selected from the group consisting of PD-L1 having the amino acid sequence as found in SEQ ID NO 13 and a protein that shares at least 80% sequence identity therewith. In particular other embodiments, PD-L1 is selected from the group consisting of PD-L1 having the amino acid sequence of amino acids 19 to 238 of SEQ ID NO 13 and a protein that shares at least 80% sequence identity therewith. Particularly, PD-L1 has the amino acid sequence as found in SEQ ID NO 1, SEQ ID NO 2 or SEQ ID NO 13, preferably PD-L1 comprises the amino acid sequence of amino acids 19 to 238 of SEQ ID NO 13. In one embodiment PD-L1 comprises at least the extracellular domain with or without the signaling peptide.

In this context, the term "about" or "approximately" means within 80% to 120%, alternatively within 90% to 110%, including within 95% to 105% of a given value or range.

In the context of the present invention, the term "protein that shares at least about 80% sequence identity with a given protein sequence, e.g., PD-L1 having the amino acid sequence as found in SEQ ID NO 1, 2 or 13" refers to a protein that may differ in the amino acid sequence and/or the nucleic acid sequence encoding the amino acid sequence of said reference protein, e.g., PD-L1 having the amino acid sequence of SEQ ID NO 1, 2 or 13. The protein may be of natural origin, e.g. a mutant version of a wild-type protein, e.g. a mutant version of a wild type PD-L1, or a homolog of a different species, or an engineered protein, e.g., engineered PD-L1. It is known that the usage of codons is different between species. Thus, when expressing a heterologous protein in a target cell, it may be necessary, or at least helpful, to adapt the nucleic acid sequence to the codon usage of the target cell. Methods for designing and constructing derivatives of a given protein are well known to anyone of ordinary skill in the art.

The protein that shares at least about 80% sequence identity with a given protein sequence, e.g., PD-L1 having the amino acid sequence as found in SEQ ID NO 1, 2 or 13, may contain one or more mutations comprising an addition, a deletion and/or a substitution of one or more amino acids in comparison to the reference protein sequence, e.g., PD-L1 having the amino acid sequence of SEQ ID NO 1, 2 or 13. The same applies to PD-L1 having the amino acid sequence of amino acids 19 to 238 of SEQ ID NO 13. The one or more mutations comprising an addition, a deletion and/or a substitution of one or more amino acids include less than 10 mutations, less than 9 mutations, less than 8 mutations, less than 7 mutations, less than 6 mutations, less than 5 mutations, less than 4 mutations, less than 3 mutations, less than 2 mutations or one mutation in the amino acid sequence of SEQ ID NO 1, 2, 13 or amino acids 19 to 238 of SEQ ID NO 13. According to the teaching of the present invention, said deleted, added and/or substituted amino acids may be consecutive amino acids or may be interspersed over the length of the amino acid sequence of the protein that shares at least about 80% sequence identity with a reference protein, e.g., PD-L1 having the amino acid sequence as found in SEQ ID NO 1, 2, 13 or amino acids 19 to 238 of SEQ ID NO 13. According to the teaching of the present invention, any number of amino acids may be added, deleted, and/or substitutes, as long as the amino acid sequence identity with the reference protein is at least about 80%. Preferably, the mutated protein is immunogenic. Preferably, the immunogenicity of the protein which shares at least about 80% sequence identity with a given reference protein, e.g., PD-L1 having the amino acid sequence as found in SEQ ID NO 1, 2, 13 or amino acids 19 to 238 of SEQ ID NO 13, is reduced by less than 50%, less than 40%, less than 30%, less than 20%, less than 10%, less than 5% or less than 1% compared to said reference protein, e.g., PD-L1 having the amino acid sequence as found in SEQ ID NO 1, 2, 13 or amino acids 19 to 238 of SEQ ID NO 13. The immunogenicity may, e.g., be measured by ELISA. Methods for designing and constructing protein homologues and for testing such homologues for their immunogenic potential are well known to anyone of ordinary skill in the art. In particular embodiments, the sequence identity with the reference protein, e.g., PD-L1 having the amino acid sequence of SEQ ID NO 1, 2, 13 or amino acids 19 to 238 of SEQ ID NO 13 is at least about 80%, at least about 85%, at least about 90%, or most particularly at least about 95%. Methods and algorithms for determining sequence identity including the comparison of a parental protein and its derivative having deletions, additions and/or substitutions relative to a parental sequence, are well known to the practitioner of ordinary skill in the art. On the DNA level, the nucleic acid sequences encoding the protein that shares at least about 80% sequence identity with a given reference protein, e.g., PD-L1 having the amino acid sequence as found in SEQ ID NO 1, 2, 13 or amino acids 19 to 238 of SEQ ID NO 13, may differ to a larger extent due to the degeneracy of the genetic code.

In particular embodiments, PD-L1 is encoded by the nucleic acid sequence as found in SEQ ID NO 3, SEQ ID NO 4 or SEQ ID NO 14.

In particular embodiments, the DNA molecule comprises the kanamycin antibiotic resistance gene, the pMB1 ori and a CMV promoter. In particular embodiments, the recombinant DNA molecule is derived from commercially available pVAX1™ expression plasmid (Invitrogen, San Diego, Calif.). This expression vector was modified by replacing the high copy pUC origin of replication by the low copy pMB1 origin of replication of pBR322. The low copy modification was made in order to reduce the metabolic burden and to render the construct more stable. The generated expression vector backbone was designated pVAX10.

In particular embodiments, the DNA molecule further comprises the DNA sequence as found in SEQ ID NO 5 (vector backbone pVAX10).

Inserting the ORF encoding human PD-L1 having the amino acid sequence of SEQ ID NO 1 into the expression vector backbone via NheI/XhoI yielded the expression plasmid pVAX10.PD-L1h. The DNA vaccine comprising the attenuated Salmonella strain Ty21a harboring the expression plasmid pVAX10.PD-L1h is designated VXM10h. Inserting the ORF encoding human PD-L1 having the amino acid sequence of SEQ ID NO 2 into the expression vector backbone via NheI/XhoI yielded the expression plasmid pVAX10.PD-L1ha. The DNA vaccine comprising the attenuated Salmonella strain Ty21a harboring the expression plasmid pVAX10.PD-L1ha is designated VXM10ha. Inserting the ORF encoding human PD-L1 having the amino acid sequence of SEQ ID NO 13 into the expression vector backbone via NheI/XhoI yielded the expression plasmid pVAX10.PD-L1 hb. The DNA vaccine comprising the attenuated Salmonella strain Ty21a harboring the expression plasmid pVAX10.PD-L1 hb is designated VXM10hb.

The attenuated strain of Salmonella encoding PD-L1 may be provided in a pharmaceutical composition. The pharmaceutical composition may be in the form of a solution, a suspension, an enteric coated capsule, a lyophilized powder or any other form suitable for the intended use.

The pharmaceutical composition may further comprise one or more pharmaceutically acceptable excipients.

In the context of the present invention, the term "excipient" refers to a natural or synthetic substance formulated alongside the active ingredient of a medication. Suitable excipients include antiadherents, binders, coatings, disintegrants, flavors, colors, lubricants, glidants, sorbents, preservatives and sweeteners.

In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

In particular embodiments, the pharmaceutical composition is provided as drinking solution. This embodiment offers the advantage of improved patient compliance and allows for rapid, feasible and affordable mass vaccination programs.

In particular, suitable drinking solutions comprise means to neutralize gastric acids to at least to a certain degree, i.e. to bring the pH of the gastric juice closer to a pH of 7. In a particular embodiment, the drinking solution is a buffered suspension obtained by suspending the attenuated strain of Salmonella according to the present invention in a suitable buffer, preferably in a buffer that neutralizes gastric acids to at least a certain degree, preferably in a buffer containing 2.6 g sodium hydrogen carbonate, 1.7 g L-ascorbic acid, 0.2 g lactose monohydrate and 100 ml of drinking water.

In a second aspect, the present invention relates to the attenuated strain of Salmonella according to the present invention for use as a medicament.

In particular embodiments, the attenuated strain of Salmonella is for use in the treatment of cancer.

In particular embodiments, the attenuated strain of Salmonella is for use as a vaccine.

In particular embodiments, the attenuated strain of Salmonella is for use in cancer immunotherapy.

Without wishing to be bound by theory, it is believed that contrary to monoclonal anti-PD-1 and anti-PD-L1 antibodies, which mediate checkpoint inhibition by preventing binding of the PD-L1 ligand to PD-1, the attenuated strain of Salmonella according to the present invention elicits a PD-L1 specific T-cell response that leads to the destruction of PD-L1-positive tumor cells. Additionally, particularly in the case of using only the extracellular domain of human PD-L1 (SEQ ID NO 13), as in the use of plasmid pVAX10.PD-L1hb, the PD-L1-based protein product being expressed may be secreted and may result in an anti-PD-L1 antibody response, which may further support the therapeutic effect of the approach according to the present invention. Without being bound by theory using truncated human PD-L1 lacking the signal peptide, e.g., truncated human PD-L1 comprising the amino acid sequence of SEQ ID NO 2, as in the use of plasmid pVAX10.PD-L1ha, and of amino acids 19 to 238 of SEQ ID NO 13 (corresponding to the extracellular domain of PD-L1), the PD-L1-based protein product being expressed may accumulate in the cytoplasm and may result in an enhanced cytotoxic T cell response against PD-L1, which may further support the therapeutic effect of the approach according to the present invention. Thus, in one embodiment the PD-L1 comprises at least the extracellular domain of PD-L1 with or without signaling peptide.

According to the invention, the attenuated Salmonella strain functions as the bacterial carrier of the recombinant DNA molecule comprising an expression cassette encoding PD-L1 for the delivery of said recombinant DNA molecule into a target cell. Such a delivery vector comprising a DNA molecule encoding a heterologous antigen, such as PD-L1, is termed DNA vaccine.

In the context of the present invention, the term "vaccine" refers to an agent which is able to induce an immune response in a subject upon administration. A vaccine can preferably prevent, ameliorate or treat a disease.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components.

Live attenuated Salmonella vectors produce their own immunomodulatory factors such as lipopolysaccharides (LPS) in situ which may constitute an advantage over other forms of administration such as microencapsulation. Moreover, the mucosal vaccine according to the present invention has an intra-lymphatic mode of action, which proves to be of benefit. After ingestion of the attenuated vaccine according to the present invention, macrophages and other cells in Peyer's patches of the gut are invaded by the modified bacteria. The bacteria are taken up by these phagocytic cells. Due to their attenuating mutations, bacteria of the S. typhi Ty21 strain are not able to persist in these phagocytic cells but die at this time point. The recombinant DNA molecules are released and subsequently transferred into the cytosol of the phagocytic immune cells, either via a specific transport system or by endosomal leakage. Finally, the recombinant DNA molecules enter the nucleus, where they are transcribed, leading to massive PD-L1 expression in the cytosol of the phagocytic cells, and potentially, particularly in the case of using only the extracellular domain of human PD-L1 (e.g., SEQ ID NO 13), as in the use of plasmid pVAX10.PD-L1 hb, in the secretion of the PD-L1-based protein product. The infected cells undergo apoptosis, loaded with the PD-L1 antigen, and are taken up and processed by the gut's immune system. The danger signals of the bacterial infection serve as a strong adjuvant in this process, leading to a strong target antigen specific CD8+ T-cell and antibody response at the level of both systemic and mucosal compartments. The immune response peaks around ten days after vaccination. The lack of anti-carrier response allows boosting with the same vaccine over many times. Additionally, the secretion of the PD-L1-based protein product may result in an anti-PD-L1 antibody response, which may further support the therapeutic effect of the approach according to the present invention.

In particular embodiments, the treatment of cancer further comprises chemotherapy, radiotherapy or biological cancer therapy. Particularly, the attenuated strain of *Salmonella* is administered before, during and/or after the chemotherapy or the radiotherapy treatment or the biological cancer therapy. More particularly, the attenuated strain of *Salmonella* is administered before and during the chemotherapy or the radiotherapy treatment or the biological cancer therapy. For cure of cancer, complete eradication of cancer stem cells may be essential. For maximal efficacy, a combination of different therapy approaches may be beneficial.

In the context of the present invention, the term "biological cancer therapy" refers to cancer therapy involving the use of living organisms including bacteria and viruses, substances derived from living organisms or laboratory-produced versions of such substances. Some biological therapies for cancer aim at stimulating the body's immune system to act against cancer cells (so called biological cancer immunotherapy). Biological cancer therapy approaches include the delivery of tumor antigens and tumor stroma antigens, e.g. by *Salmonella* based DNA vaccines, particularly *S. typhi* Ty21a based DNA vaccines, delivery of therapeutic antibodies as drugs, administration of immunostimulatory cytokines and administration of immune cells, including engineered T-cells. Therapeutic antibodies include antibodies targeting tumor antigens or tumor stroma antigens.

In particular embodiments, the biological cancer therapy comprises administration of at least one further DNA vaccine encoding a tumor antigen and/or a tumor stroma antigen. In particular embodiments, the at least one further DNA vaccine is selected from at least one further attenuated strain of *Salmonella* comprising at least one copy of a DNA molecule comprising an expression cassette encoding a tumor antigen and/or a tumor stroma antigen. Particularly, said at least one further attenuated strain of *Salmonella* is *Salmonella typhi* Ty21a comprising a eukaryotic expression cassette.

In one embodiment said tumor antigen is selected from Wilms' Tumor Protein (WT1), Mesothelin (MSLN), CEA and CMV pp65. In particular embodiments, said tumor antigen encoded by said at least one further DNA vaccine is selected from the group consisting of Wilms' Tumor Protein (WT1) having the amino acid sequence as found in SEQ ID NO 6 and a protein that shares at least about 80% sequence identity therewith, Mesothelin (MSLN) having the amino acid sequence as found in SEQ ID NO 7 and a protein that shares at least about 80% sequence identity therewith, CEA having the amino acid sequence as found in SEQ ID NO 8 and a protein that shares at least about 80% sequence identity therewith, CMV pp65 having the amino acid sequence as found in SEQ ID NO 9 and a protein that shares at least about 80% sequence identity therewith, CMV pp65 having the amino acid sequence as found in SEQ ID NO 10 and a protein that shares at least about 80% sequence identity therewith, and CMV pp65 having the amino acid sequence as found in SEQ ID NO 11 and a protein that shares at least about 80% sequence identity therewith. Particularly, Wilms' Tumor Protein (WT1) has the amino acid sequence as found in SEQ ID NO 6, Mesothelin (MSLN) has the amino acid sequence as found in SEQ ID NO 7, CEA has the amino acid sequence as found in SEQ ID NO 8, and CMV pp65 has the amino acid sequence as found in SEQ ID NO 9, SEQ ID NO 10 or SEQ ID NO 11. In one embodiment said tumor stroma antigen is VEGFR-2 or FAP, preferably VEGFR-2. Particularly, said tumor stroma antigen encoded by said at least one further DNA vaccine is selected from the group consisting of VEGFR-2 having the amino acid sequence as found in SEQ ID NO 12 and a protein that shares at least about 80% sequence identity therewith and human fibroblast activation protein (FAP). Particularly, VEGFR-2 has the amino acid sequence as found in SEQ ID NO 12.

In particular embodiments, the attenuated strain of *Salmonella* encoding PD-L1 is administered prior to, simultaneously with and/or after the at least one further DNA vaccine encoding a tumor antigen and/or a tumor stroma antigen.

In the context of the present invention, the term "simultaneously with" means administration of the attenuated strain of *Salmonella* encoding PD-L1 and the at least one further DNA vaccine encoding a tumor antigen and/or a tumor stroma antigen on the same day, more particularly within 12 hours, more particularly within 2 hours.

In particular embodiments, administration of the attenuated *Salmonella* strain encoding PD-L1 and the at least one further DNA vaccine encoding a tumor antigen and/or a tumor stroma antigen occurs within twelve consecutive weeks, more particularly within eight consecutive weeks, more particularly within three to six consecutive weeks. The attenuated *Salmonella* strain encoding PD-L1 and the at least one further DNA vaccine encoding a tumor antigen and/or a tumor stroma antigen may be administered via the same route or via different routes. For example, in particular if the at least one further DNA vaccine is a further attenuated strain of *Salmonella*, it may be administered orally.

The single dose of the further attenuated strain of *Salmonella* may comprise from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

Chemotherapeutic agents that may be used in combination with the attenuated mutant strain of *Salmonella* of the present invention may be, for example gemcitabine, amifostine (ethyol), cabazitaxel, carboplatin, oxaliplatin, cisplatin, capecitabine, dacarbazine (DTIC), dactinomycin, docetaxel, mechlorethamine, streptozocin, cyclophosphamide, nimustine (ACNU), carmustine (BCNU), lomustine (CCNU), doxorubicin (adriamycin), doxorubicin lipo (doxil), folinic acid, gemcitabine (gemzar), daunorubicin, daunorubicin lipo (daunoxome), epirubicin, procarbazine, ketoconazole, mitomycin, cytarabine, etoposide, methotrexate, 5-fluorouracil (5-FU), vinblastine, vincristine, bleomycin, paclitaxel (taxol), docetaxel (taxotere), permetrexed, aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, temozolomide and combinations thereof.

Most preferred chemotherapeutic agents according to the invention are cabazitaxel, carboplatin, oxaliplatin, cisplatin, cyclophosphamide, docetaxel, etoposide, gemcitabine, doxorubicin, lomustine, paclitaxel (taxol), irinotecan, vincristine, vinblastine, vinorelbin, folinic acid, 5-fluorouracil, bleomycin and temozolomide, especially gemcitabine.

In particular embodiments, the attenuated strain of Salmonella is administered orally. Oral administration is simpler, safer and more comfortable than parenteral administration. However, it has to be noted that the attenuated strain of Salmonella encoding PD-L1 may also be administered by any other suitable route. Preferably, a therapeutically effective dose is administered to the subject, and this dose depends on the particular application, the type of malignancy, the subject's weight, age, sex and state of health, the manner of administration and the formulation, etc. Administration may be single or multiple, as required.

In particular embodiments, the cancer is selected from lymphoma, leukemia, myeloma, lung cancer, in particular non-small cell lung cancer (NSCLC), melanoma, renal cell cancer, ovarian cancer, glioblastoma, merkel cell carcinoma, bladder cancer, head and neck cancer, colorectal cancer, esophagial cancer, cervical cancer, gastric cancer, hepatocellular cancer, prostate cancer, breast cancer, pancreatic cancer, and thyroid cancer.

The attenuated strain of Salmonella encoding PD-L1 is surprisingly effective at relatively low doses. Administration of low doses of live bacterial vaccines minimizes the risk of excretion and thus of transmission to third parties.

In particular embodiments, the single dose of the attenuated strain of Salmonella comprises from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In this context, the term "about" or "approximately" means within a factor of 3, alternatively within a factor of 2, including within a factor of 1.5 of a given value or range.

In particular embodiments, the attenuated strain of Salmonella is for use in individualized cancer immunotherapy comprising the step of assessing the PD-L1 expression pattern and/or the pre-immune response against PD-L1 of a patient. The patient's PD-L1 expression and/or the patient's pre-immune responses against PD-L1 may be assessed in a first step for example by companion diagnostics. Methods for assessing the expression of a target gene, such as PD-L1, either on mRNA or on protein level are well known to any one of ordinary skill in the art. For instance, immunohistochemistry staining, flow cytometry methods or RNA sequencing, or alternative methods using labelling can be used to identify the level of target expression in the tumor. Similarly, methods for assessing a patient's pre-immune response against a given protein, such as PD-L1, are well known to any one of ordinary skill in the art. A patient's pre-existing PD-L1 specific T-cell pool can be detected by e.g. ELISpot or multimer FACS analysis. High tumor-specific PD-L1 expression and/or the occurrence of pre-immune responses against PD-L1 are prognostic indicators for the predisposition of a patient to respond especially favorably to the treatment with the attenuated strain of Salmonella encoding PD-L1.

The attenuated strain of Salmonella encoding PD-L1 may be provided in the form of a solution, a suspension, a lyophilisate, an enteric coated capsule, or any other suitable form. Typically, the attenuated strain of Salmonella is formulated as drinking solution. This embodiment offers the advantage of improved patient compliance. Preferably, the drinking solution comprises means to neutralize gastric acids at least to a certain degree, i.e. to bring the pH of the gastric juice closer to a pH of 7. Preferably, the drinking solution is a buffered suspension comprising the attenuated strain of Salmonella encoding PD-L1. In a particular embodiment, the buffered suspension is obtained by suspending the attenuated strain of Salmonella in a suitable buffer, preferably containing 2.6 g sodium hydrogen carbonate, 1.7 g L-ascorbic acid, 0.2 g lactose monohydrate and 100 ml of drinking water.

It may be favorable dependent on the occurrence of possible side effects, to include treatment with antibiotics or anti-inflammatory agents.

Should adverse events occur that resemble hypersensitivity reactions mediated by histamine, leukotrienes, or cytokines, treatment options for fever, anaphylaxis, blood pressure instability, bronchospasm, and dyspnoea are available. Treatment options in case of unwanted T-cell derived auto-aggression are derived from standard treatment schemes in acute and chronic graft vs. host disease applied after stem cell transplantation. Cyclosporin and glucocorticoids are proposed as treatment options.

In the unlikely case of systemic Salmonella typhi Ty21a type infection, appropriate antibiotic therapy is recommended, for example with fluoroquinolones including ciprofloxacin or ofloxacin. Bacterial infections of the gastrointestinal tract are to be treated with respective agents, such as rifaximin.

In particular embodiments, cancer immunotherapy comprises a single or multiple administrations of the attenuated strain of Salmonella PD-L1 or a pharmaceutical composition comprising the same. The single dose of the administrations may be the same or different. In particular, cancer immunotherapy comprises 1, 2, 3, 4, 5 or 6 administrations of the attenuated strain of Salmonella encoding PD-L1, preferably wherein the multiple administrations occur within three to six consecutive months.

SHORT DESCRIPTION OF FIGURES

FIG. 1: Amino acid sequence of human full length PD-L1 (SEQ ID NO 1), which is encoded by PD-L1 cDNA contained in plasmid pVAX10.PD-L1h.

FIG. 2: Amino acid sequence of a truncated form of human PD-L1 (SEQ ID NO 2) lacking the signaling peptide (MRIFAVFIFMTYWHLLNA; SEQ ID NO 19), which is encoded by PD-L1 cDNA contained in plasmid pVAX10.PD-L1ha.

FIG. 3: Nucleic acid sequence (SEQ ID NO 3) contained in plasmid pVAX10.PD-L1h and encoding human full length PD-L1 of SEQ ID NO 1.

FIG. 4: Nucleic acid sequence (SEQ ID NO 4) contained in plasmid pVAX10.PD-L1ha and encoding truncated human PD-L1 of SEQ ID NO 2.

FIG. 5: Nucleic acid sequence comprised in empty expression vector pVAX10 (sequence of expression vector pVAX10 without the portion of the multiple cloning site which is located between the restriction sites NheI and XhoI (SEQ ID NO 5).

FIG. 6: Amino acid sequence of human WT1 encoded by WT1 cDNA contained in plasmid pVAX10.hWT1 (SEQ ID NO 6).

FIG. 7: Amino acid sequence of human MSLN encoded by MSLN cDNA contained in plasmid pVAX10.hMSLN (SEQ ID NO 7).

FIG. 8: Amino acid sequence of human CEA encoded by CEA cDNA contained in plasmid pVAX10.hCEA (SEQ ID NO 8).

FIG. 9: Amino acid sequence of CMV pp65 encoded by CMV pp65 cDNA contained in plasmid pVAX10.CMVpp65_1 (SEQ ID NO 9).

FIG. 10: Amino acid sequence of CMV pp65 encoded by CMV pp65 cDNA contained in plasmid pVAX10.CMVpp65_2 (SEQ ID NO 10).

FIG. 11: Amino acid sequence of CMV pp65 encoded by CMV pp65 cDNA contained in plasmid pVAX10.CMVpp65_3 (SEQ ID NO 11).

FIG. 12: Amino acid sequence of VEGFR-2 encoded by VEGFR-2 cDNA contained in plasmid pVAX10.VR2-1 (SEQ ID NO 12).

FIG. 13: Amino acid sequence of truncated human PD-L1 (SEQ ID NO 13) comprising the extracellular domain (amino acids 19-238) and the signaling peptide (amino acids 1-18).

FIG. 14: Nucleic acid sequence (SEQ ID NO 14) encoding the truncated human PD-L1 of SEQ ID NO 13.

FIG. 15: Effects of the prophylactic administration of VXM10m and VXM10ma on the survival of C57BL/6 mice bearing disseminated syngeneic FBL-3 erythroleukemia. Mice were vaccinated with (A) empty vector (1.6×10$^8$ CFU); (B) VXM10m (1.8×10$^8$ CFU); (C) VXM10m (1.0×10$^{10}$ CFU); (D) VXM10ma (3.6×10$^8$ CFU); or (E) VXM10ma (1.0×10$^{10}$ CFU). The vertical arrow indicates tumor inoculation.

Figure 16:
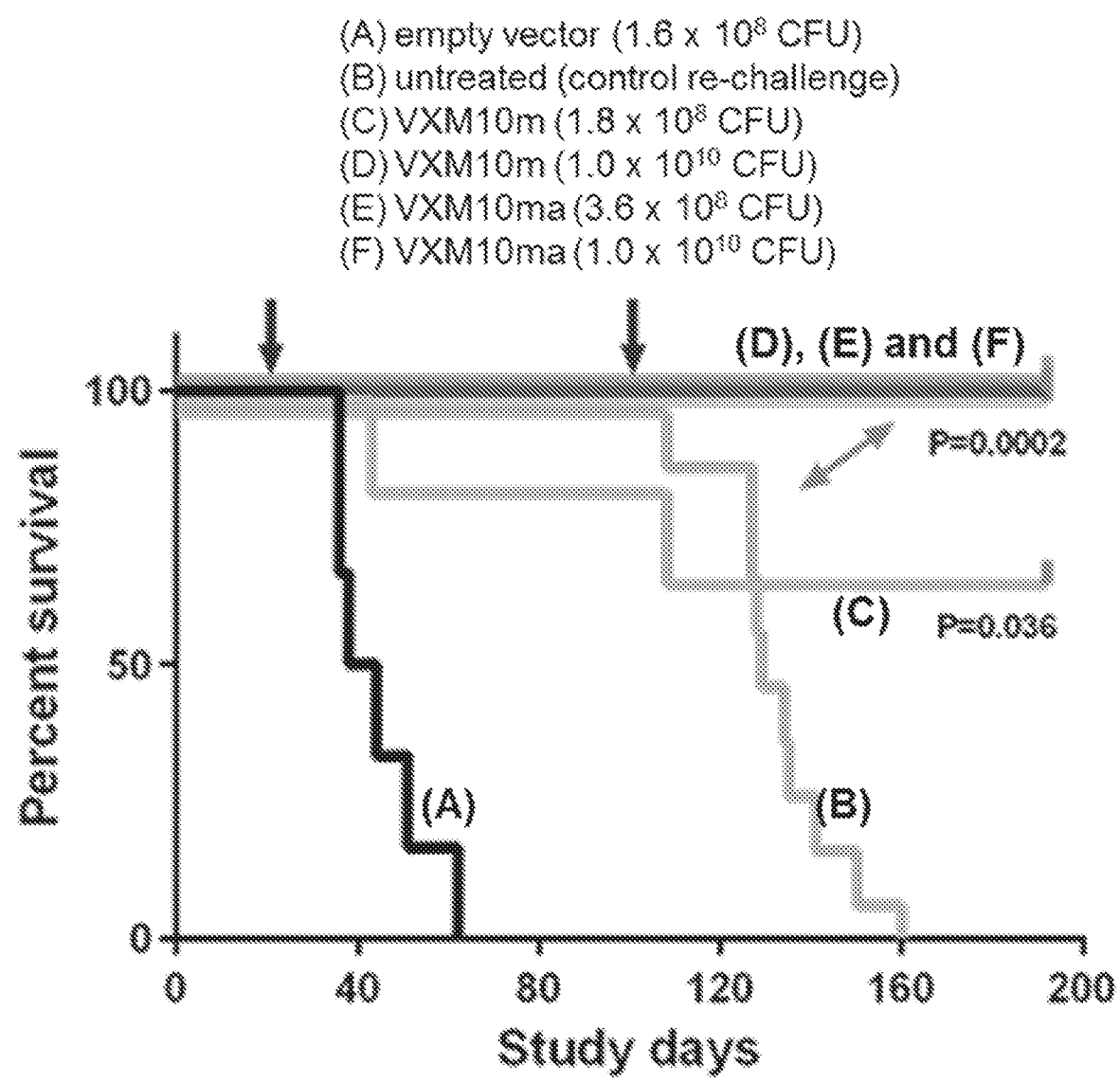

FIG. 16: Effects of the prophylactic administration of VXM10m and VXM10ma on long-term survival of C57BL/6 mice after re-challenge with FBL-3 cells. Mice were vaccinated and treated as follows (A) empty vector (1.6×10$^8$ CFU); (B) untreated (control re-challenge); (C) VXM10m (1.8×10$^8$ CFU); (D) VXM10m (1.0×10$^{10}$ CFU); (E) VXM10ma (3.6×10$^8$ CFU); or (F) VXM10ma (1.0×10$^{10}$ CFU). The vertical arrows indicate tumor inoculation.

FIG. 17: Effects of the therapeutic administration of VXM10 m and VXM10ma on the survival of C57BL/6 mice bearing disseminated syngeneic FBL-3 erythroleukemia. A) Schedule for the therapeutic vaccination with VXM10m and VXM10ma in the FBL-3 model. B) Mice were vaccinated with (A) empty vector (1.0×10$^9$ CFU); (B) VXM10m (1.0×10$^9$ CFU); or (C) VXM10ma (1.0×10$^9$ CFU). The vertical arrow indicates tumor inoculation.

FIG. 18: (A) Experimental design, and (B) anti-PD-L1 response in the sera of C57BL/6 mice bearing disseminated syngeneic FBL-3 erythroleukemia, collected 79 days after the final vaccination (vaccination schedule: d1, d3, d5, d7, d14, d21; FBL-3 challenge d20) with VXM10 10$^8$ CFU (square), VXM10 10$^{10}$ CFU (circle), VXM10a 10$^8$ CFU (triangle, tip down), VXM10a 10$^{10}$ CFU (triangle, tip up), negative control (rectangle). The dashed line represents the cut-off value derived from the values of the negative control group (95% confidence). Soluble recombinant murine PD-L1 was used for immunization with CFA/IFA in the positive control group (cross).

FIG. 19: (A) Experimental design, and (B) level of IFNγ (open symbols) and TNFα (closed symbols) secreted by splenocytes isolated from mice immunized with the empty vector (circles), VXM10 (squares) or VXM10a (triangles), and stimulated with a pool of 5 peptides derived from PD-L1, as measured in the culture supernatant by ELISA after 6 days of stimulation (mean of n=5).

EXAMPLES

Example 1: Assessment of the Antitumor Activity of VXM10m in C57BL/6 Mice Bearing Disseminated Syngeneic FBL-3 Erythroleukemia The aim of this study was to investigate the antitumor efficacy of two *Salmonella* based PD-L1 DNA vaccines in C57 BL/6 mice bearing disseminated syngeneic FBL-3 erythroleukemia. VXM10m is *Salmonella typhimurium* aroA strain SL7207 transformed with expression plasmid pVAX10 encoding murine full-length native PD-L1 (with the nucleic acid sequence of SEQ ID NO 17). VXM10ma is *Salmonella typhimurium* aroA strain SL7207 transformed with expression plasmid pVAX10 encoding a truncated form of murine PD-L1 (with the nucleic acid sequence of SEQ ID NO 18), more specifically the N-terminus truncated by 17 amino acid residues.

The treatment started the day of randomization that was considered as day 1 (D1). Thirty healthy male C57BL/6 mice, 4-6 weeks old, were randomized according to their body weight into 5 groups of 6 animals each. Animal allocation to treatment groups is summarized in Table 1. A statistical test (Student t test) was performed to test for homogeneity between the groups (data not shown).

TABLE 1

| Group # | No. Animals | Vaccine | Dose | Route | Treatment Schedule |
|---|---|---|---|---|---|
| 1 | 6 | Empty vector (VXM0m_empty) | 1.6 × 10$^8$ CFU/adm | p.o. | d1, d3, d5, d7, d14, d21 |
| 2 | 6 | VXM10m (PD-L1 full-length) | 1.8 × 10$^8$ CFU/adm | p.o. | d1, d3, d5, d7, d14, d21 |
| 3 | 6 | VXM10m-HD (high-dose) | 1.0 × 10$^{10}$ CFU/adm | p.o. | d1, d3, d5, d7, d14, d21 |
| 4 | 6 | VXM10ma (PD-L1 truncated) | 3.6 × 10$^8$ CFU/adm | p.o. | d1, d3, d5, d7, d14, d21 |
| 5 | 6 | VXM10ma-HD (high-dose) | 1.0 × 10$^{10}$ CFU/adm | p.o. | d1, d3, d5, d7, d14, d21 |

Group 1 was treated with the empty vector control (VXM0m_empty; *S. typhimurium* bacterial vector control harboring no exogenous expression plasmid). Groups 2 to 5 were treated with VXM10m or VXM10ma, at two different single doses.

VXM0m-empty, VXM10m and VXM10ma were administered by oral gavage (per os, po) in 100 μl in final volumes per application. Regardless of animal groups, each animal received pre-dose application buffer po to neutralize acid in the stomach prior dosing (100 μl/animal/application). This buffer was produced by dissolution of 2.6 g sodium hydrogen carbonate, 1.7 g L-Ascorbic acid, 0.2 g lactose monohydrate in 100 ml of drinking water and was applied within 30 min prior application of VXM0m-empty, VXM10m and VXM10ma.

Prime vaccination started at day 1 and consisted of 4 administrations every second day (d1, 3, 5, 7). Prime vaccination was followed by two boost vaccinations at days 14 and 21.

Tumors were induced in all animals by I.P. injection of 5.0×10⁶ FBL-3 cells in 500 µl RPMI 1640 on day 20. FBL-3 is a Friend leukemia virus-induced erythroleukemia cell line originated from C57BL/6 mice. This cell line expresses unique tumor specific transplantation antigens that can be recognized by the immune system. Priming syngeneic mice with FBL-3 tumor cells leads to the subsequent rejection of future live tumor challenges. Although FBL-3 is immunogenic, injection of live FBL-3 tumor cells into naïve syngeneic mice results in tumor growth, suggesting that the FBL-3 tumor cells possess mechanisms of escaping immune recognition and destruction. Of note, PD-L1 was shown to be highly expressed on the FBL-3 cell line.

Animal body weight, viability and animal behavior were monitored throughout the study.

Survival of test animals is displayed in a Kaplan-Meier plot in FIG. 15.

Example 2: Effects of the Administration of VXM10m and VXM10ma on the Long-Term Survival of C57BL/6 Mice after Re-Challenge with FBL-3 Cells The aim of this study was to investigate the long-term effect of antitumor efficacy of two *Salmonella* based PD-L1 DNA vaccines in C57 BL/6 mice bearing disseminated syngeneic FBL-3 erythroleukemia following re-challenge.

The Study of Example 1 was continued and mice were receiving a second tumor induction dose on day 100. Further unvaccinated control animals (n=10) that were present in the study from the start of the experiment, but received no first tumor induction, were included as a control for the tumor re-challenge. Re-challenge was performed by tumor induction in all animal of Groups 2-5 (see Table 1) and the unvaccinated control animals by I.P. injection of 5.0×10⁶ FBL-3 cells in 500 µl RPMI 1640 on day 100.

Animal body weight, viability and animal behavior were continuously monitored. Over the treatment phase, when compared with control group, administration of VXM10m and VXM10ma generated a potent memory T cell response against the leukemia, with 100% of long-term surviving mice also after re-challenge with FBL-3 cells. No vaccination-related toxicity or body weight loss was observed throughout the study. Survival of test animals is displayed in a Kaplan-Meier plot in FIG. 16.

Example 3: Assessment of the Therapeutic Antitumor Activity of VXM10m and VXM10ma in C57BL/6 Mice Bearing Disseminated Syngeneic FBL-3 Erythroleukemia The aim of this study was to investigate the antitumor efficacy of VXM10m and VXM10ma administered therapeutically in C57BL/6 mice bearing disseminated syngeneic FBL-3 erythroleukemia.

Tumors were induced in all animals by intraperitoneal (i.p.) injection of 5.0×10⁶ FBL-3 cells in 500 µl RPMI 1640 on day 0.

The treatment started the day of randomization that was considered as day 1 (D1, after tumor injection). For the treatment groups sixteen healthy male C57BL/6 mice, 4-6 weeks old, were randomized according to their body weight into 2 groups of 8 animals each. A statistical test (Student t test) was performed to test for homogeneity between the groups (data not shown).

VXM0m-empty, VXM10m and VXM10ma were administered by oral gavage (per os, po) at $1.0 \times 10^9$ CFU in 100 µl as described in Example 1.

One group of 8 mice was treated with the empty vector control (VXM0m_empty; *S. typhimurium* bacterial vector control harboring no exogenous expression plasmid). The other group of 8 mice were treated with VXM10m or VXM10ma, with a prime treatment 4 times on Days 1, 3, 5, 7 and 2 weekly boosts on Days 14 and 21 (FIG. 17A).

Animal body weight, viability and animal behavior were monitored 3 times weekly during the prime-boost period and upon the peak immune response, i.e., from study day 0 to 28, and then twice weekly until the end of the study.

Over the treatment phase, when compared with control group, oral administration of VXM10m and VXM10ma resulted a strong anti-tumor effect in the FBL-3 leukemia model, with 100% of surviving animals 80 days after leukemia challenge (FIG. 17B). No vaccination-related toxicity or body weight loss was observed throughout the study. Administration of the empty vector did not show any anti-cancer effect.

Example 4: Assessment of the Anti-PD-L1 Antibody Response Following Vaccination with VXM10m and VXM10ma in C57BL/6 Mice Bearing Disseminated Syngeneic FBL-3 Erythroleukemia The aim of this study was to investigate the anti-PD-L1 response to VXM10 or VXM10a administered at $10^8$ CFU and $10^{10}$ CFU at days 1, 3, 5 and 7 with a boost at days 14 and 21 in C57 BL/6 mice bearing disseminated syngeneic FBL-3 erythroleukemia. Tumors were induced in all animals by I.P. injection of $5.0 \times 10^6$ FBL-3 cells on day 20. Vaccination and tumor induction was performed basically as described in Example 1. Soluble recombinant murine PD-L1 was used for immunization with CFA/IFA in the positive control group.

The systemic antibody response was evaluated by ELISA in the serum of animals vaccinated with either VXM10 or VXM10a, 79 days after the final vaccination on day 21 (FIG. 18A). Anti-PD-L1 antibodies were detected in a few animals vaccinated with VXM10 and VXM10a, and the response was more pronounced in the highest dose treatment groups, with 50% of the animals (3 out of 6) showing a signal-to-background ration above the cut-off value (FIG. 18B)

Example 5: Assessment of the T-Cell Response Against PD-L1 Following Vaccination with VXM10m and VXM10ma in C57BL/6 Mice The aim of this study was to investigate the T-cell response induced against PD-L1 epitopes in healthy C57 BL/6 mice (n=5 per group) immunized four times every other day (days 1, 3, 5 and 7) via oral route with $10^{10}$ CFU of either VXM10, VXM10a or the empty vector control (FIG. 19A).

Ex vivo restimulation of the spenocytes was performed 10 days after the last immunization (day 17), using a pool of 5 immunogenic peptides derived from murine PD-L1. The content of the culture supernatant was tested for the presence of IFNγ and TNFα by ELISA after 6 days of in vitro stimulation.

The level of TNFα, and to a lesser extend IFNγ, was significantly increased in the supernatant of spenocytes derived from animals vaccinated with VXM10a and stimulated with PD-L1 peptides (FIG. 19B). These data confirm that immunization with VXM10a induced a pool of T-cells specific for PD-L1.

Example 6: Assessment of the Antitumor Activity of VXM10mb in C57BL/6 Mice Bearing Disseminated Syngeneic FBL-3 Erythroleukemia The aim of this study is to investigate the long-term effect of antitumor efficacy of a third *Salmonella* based PD-L1 DNA vaccines in C57 BL/6 mice bearing disseminated syngeneic FBL-3 erythroleukemia. VXM10mb is *Salmonella typhimurium* aroA strain SL7207 transformed with expression plasmid pVAX10 encoding a truncated form of murine PD-L1, more specifically the extracellular domain including the N-terminal signaling peptide (amino acid sequence SEQ ID NO 15; nucleic acid sequence SEQ ID NO 16). The Experiment is essentially performed as described in Examples 1 and 2.

Example 7: Assessment of the Therapeutic Antitumor Activity of VXM10mb in C57BL/6 Mice Bearing Disseminated Syngeneic FBL-3 Erythroleukemia The aim of this study is to investigate the antitumor efficacy of VXM10mb administered therapeutically in C57BL/6 mice bearing disseminated syngeneic FBL-3 erythroleukemia. The Experiment is essentially performed as described in Example 3.

The invention claimed is:

1. A method of treating cancer in a cancer patient, comprising administering orally to the cancer patient an effective amount of an attenuated strain of *Salmonella* comprising at least one copy of a DNA molecule comprising a eukaryotic expression cassette encoding PD-L1, wherein the
    PD-L1 is a protein comprising an amino acid sequence as set forth in SEQ ID NO: 1 or an amino acid sequence having at least 80% sequence identity with SEQ ID NO: 1, wherein
    immunogenicity of the protein comprising the amino acid sequence having at least 80% sequence identity with SEQ ID NO: 1 is reduced by less than 50% when compared to the immunogenicity of the protein comprising the amino acid sequence as set forth in SEQ ID NO: 1; and wherein
    the cancer comprises PD-L1-positive tumor cells and the immunogenicity of the protein is PD-L1-specific immunogenicity.

2. The method of claim 1, wherein the attenuated strain of *Salmonella* provides anti-cancer immunotherapy to the cancer patient.

3. The method of claim 1, wherein the method further comprises administering chemotherapy, radiotherapy or biological cancer therapy, wherein the attenuated strain of *Salmonella* is administered before, during and/or after the chemotherapy or the radiotherapy or the biological cancer therapy.

4. The method of claim 3, wherein the method further comprises administering biological cancer therapy, which comprises administering at least one further DNA vaccine encoding a tumor antigen and/or a tumor stroma antigen.

5. The method of claim 4, wherein the at least one further DNA vaccine comprises an attenuated strain of *Salmonella typhi* Ty21a comprising a eukaryotic expression cassette.

6. The method of claim 4, wherein the at least one further DNA vaccine encodes a tumor antigen selected from the group consisting of Wilms' Tumor Protein (WT1), Mesothelin (MSLN), carcinoembryonic antigen (CEA), and CMV pp65, and/or encodes a tumor stroma antigen selected from the group consisting of VEGFR-2 and human fibroblast activation protein (FAP).

7. The method of claim 6, wherein the at least one further DNA vaccine encodes a tumor antigen selected from the group consisting of Wilms' Tumor Protein (WT1) having the amino acid sequence as set forth in SEQ ID NO: 6, Mesothelin (MSLN) having the amino acid sequence as set forth in SEQ ID NO: 7, CEA having the amino acid sequence as set forth in SEQ ID NO: 8, CMV pp65 having the amino acid sequence as set forth in SEQ ID NO: 9, CMV pp65 having the amino acid sequence as set forth in SEQ ID NO: 10, and CMV pp65 having the amino acid sequence as set forth in SEQ ID NO: 11; and wherein the at least one further DNA vaccine encodes a tumor stroma antigen selected from the group consisting of VEGFR-2 having the amino acid sequence as set forth in SEQ ID NO: 12, and human fibroblast activation protein (FAP).

8. The method of claim 1, wherein the cancer is selected from lymphoma, leukemia, myeloma, lung cancer, non-small cell lung cancer (NSCLC), melanoma, renal cell cancer, ovarian cancer, glioblastoma, merkel cell carcinoma, bladder cancer, head and neck cancer, colorectal cancer, esophageal cancer, cervical cancer, gastric cancer, hepatocellular cancer, prostate cancer, breast cancer, pancreatic cancer, and thyroid cancer.

9. The method of claim 1, wherein a single dose of the attenuated strain of *Salmonella* comprises from about $10^5$ to about $10^{11}$ colony forming units (CFU) of the strain.

10. The method of claim 1, further comprising assessing the cancer patient's PD-L1 expression pattern and/or pre-immune response against the PD-L1 before and/or after the treatment with the attenuated strain of *Salmonella*.

11. The method of claim 1, wherein the PD-L1 comprises an amino acid sequence that shares at least 90% sequence identity with SEQ ID NO: 1.

12. The method of claim 8, wherein the cancer is glioblastoma.

13. The method of claim 6, wherein the at least one further DNA vaccine encodes VEGFR-2.

14. The method of claim 13, wherein the at least one further DNA vaccine comprises a *S. typhi* Ty21a encoding the VEGFR-2, wherein the VEGFR-2 comprises the amino acid sequence of SEQ ID NO: 12.

* * * * *

UNITED STATES PATENT AND TRADEMARK OFFICE
CERTIFICATE OF CORRECTION

| | | |
|---|---|---|
| PATENT NO. | : 11,357,842 B2 | Page 1 of 1 |
| APPLICATION NO. | : 16/494629 | |
| DATED | : June 14, 2022 | |
| INVENTOR(S) | : Lubenau | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 9 days.

Signed and Sealed this
Eleventh Day of February, 2025

Coke Morgan Stewart
*Acting Director of the United States Patent and Trademark Office*